(12) United States Patent
Cooke et al.

(10) Patent No.: US 6,451,558 B1
(45) Date of Patent: Sep. 17, 2002

(54) GENES IN THE CONTROL OF HEMATOPOIESIS

(75) Inventors: Michael Paul Cooke, Del Mar; Claire Louise Holness, Palo Alto; Oksana Ivanivna Sirenko, Belmont, all of CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/362,123

(22) Filed: Jul. 27, 1999

Related U.S. Application Data

(60) Provisional application No. 60/155,232, filed on Aug. 3, 1998, now abandoned.

(51) Int. Cl.[7] .......................... C12P 21/06; C12N 15/63; C12N 5/00; C12N 5/08; C07H 21/04
(52) U.S. Cl. ................... 435/69.1; 435/320.1; 435/325; 435/370; 435/375; 435/455; 536/23.1; 536/23.5
(58) Field of Search .................. 435/60.1, 325, 435/320.1, 370, 375, 455; 536/23.1, 23.5

(56) References Cited

FOREIGN PATENT DOCUMENTS

| WO | WO 98 42741 A | 1/1998 |
|---|---|---|
| WO | WO 98 12306 A | 3/1998 |
| WO | WO 98 39448 A | 9/1998 |
| WO | WO 98 45436 A | 10/1998 |

OTHER PUBLICATIONS

Yu et.al.; Large–Scale Concatenation cDNA Sequencing, 1997, Genome Research 7:353–358.*
Perrotti et al. Overexpression of the Zinc Finger Protein MZF1 Inhibits Hematoporetic Development from Embryonic Stem Cells: Correlation with Negative Regulation of CD34 and C–myb Promoter Activity Mol. Cell Biol. 15:6075–6087, 1995.*
Ngo et al. In Merz et al. (ed.) "The protein folding problem and teritiary structure prediction", Birkhauser, pp. 491–495, 1994.*
Rudinger, J. In J.A. Parsons (ed.) "Peptide hormones", University Park Press, pp. 1–7, 1976.*

* cited by examiner

*Primary Examiner*—Dave T. Nguyen
*Assistant Examiner*—Quang Nguyen
(74) *Attorney, Agent, or Firm*—Douglas A. Golightly; Thomas Hoxie; Geoffrey M. Karny

(57) ABSTRACT

The present invention provides three novel HSC genes designated SCM 3, SCM 26, and SCM 113, the coding regions thereof, the gene products, applications of the genes, DNA constructs, vectors and transformed cells each comprising the gene of a fragment thereof. Methods of using the SCM 3, SCM 26 and SCM 113 polynucleotide and polypeptide sequences are also disclosed.

15 Claims, 15 Drawing Sheets

Nucleotide sequence of SCM26

```
             10         20         30         40         50         60
     CGGGGACCGA GCATTTCAGA TCTGCTCGGT AGACCTGGTG CACCACCACC ATGTTGGCTG
                                                            M  L  A>

70         80         90        100        110        120
     CAAGGCTGGT GTGTCTCCGG ACACTACCTT CTAGGGTTTT CCACCCAGCT TTCACCAAGG
     A  R  L   V  C  L  R   T  L  P   S  R  V  F   H  P  A   F  T  K>

130        140        150        160        170        180
     CCTCCCCTGT TGTGAAGAAT TCCATCACGA AGAATCAATG GCTGTTAACA CCTAGCAGGG
     A  S  P   V  V  K  N   S  I  T   K  N  Q  W   L  L  T   P  S  R>

190        200        210        220        230        240
     AATATGCCAC CAAAACAAGA ATTGGGATCC GGCGTGGGAG AACTGGCCAA GAACTCAAAG
     E  Y  A  T   K  T  R   I  G  I   R  R  G  R   T  G  Q   E  L  K>

250        260        270        280        290        300
     AGGCAGCATT GGAACCATCG ATGGAAAAAA TATTTAAAAT TGATCAGATG GGAAGATGGT
     E  A  A  L   E  P  S   M  E  K   I  F  K  I   D  Q  M   G  R  W>

310        320        330        340        350        360
     TTGTTGCTGG AGGGGCTGCT GTTGGTCTTG GAGCATTGTG CTACTATGGC TTGGGACTGT
     F  V  A  G   G  A  A   V  G  L   G  A  L  C   Y  Y  G   L  G  L>

370        380        390        400        410        420
     CTAATGAGAT TGGAGCTATT GAAAAGGCTG TAATTTGGCC TCAGTATGTC AAGGATAGAA
     S  N  E  I   G  A  I   E  K  A   V  I  W  P   Q  Y  V   R  D  R>

430        440        450        460        470        480
     TTCATTCCAC CTATATGTAC TTAGCAGGGA GTATTGGTTT AACAGCTTTG TCTGCCATAG
     I  H  S  T   Y  M  Y   L  A  G   S  I  G  L   T  A  L   S  A  I>

490        500        510        520        530        540
     CAATCAGCAG AACGCCTGTT CTCATGAACT TCATGATGAG AGGCTCTTGG GTGACAATTG
     A  I  S  R   T  P  V   L  M  N   F  M  M  R   G  S  W   V  T  I>

550        560        570        580        590        600
     GTGTGACCTT TGCAGCCATG GTTGGAGCTG GAATGCTGGT ACGATCAATA CCATATGACC
     G  V  T  F   A  A  M   V  G  A   G  M  L  V   R  S  I   P  Y  D>

610        620        630        640        650        660
     AGAGCCCAGG CCCAAAGCAT CTTGCTTGGT TGCTACATTC TGGTGTGATG GGTGCAGTGG
     Q  S  P  G   P  K  H   L  A  W   L  L  H  S   G  V  M   G  A  V>

670        680        690        700        710        720
     TGGCTCCTCT GACAATATTA GGGGGTCCTC TTCTCATCAG AGCTGCATGG TACACAGCTG
     V  A  P  L   T  I  L   G  G  P   L  L  I  R   A  A  W   Y  T  A>
```

FIG.2A

```
         730        740        750        760        770        780
GCATTGTGGG AGGCCTCTCC ACTGTGGCCA TGTGTGCGCC CAGTGAAAAG TTTCTGAACA
 G  I  V  G  G  L  S  T  V  A  M  C  A  P  S  E  K  F  L  N>

790        800        810        820        830        840
TGGGTGCACC CCTGGGAGTG GGCCTGGGTC TCGTCTTTGT GTCCTCATTG GGATCTATGT
 M  G  A  P  L  G  V  G  L  G  L  V  F  V  S  S  L  G  S  M>

850        860        870        880        890        900
TTCTTCCACC TACCACCGTG GCTGGTGCCA CTCTTTACTC AGTGGCAATG TACGGTGGAT
 F  L  P  P  T  T  V  A  G  A  T  L  Y  S  V  A  M  Y  G  G>

910        920        930        940        950        960
TAGTTCTTTT CAGCATGTTC CTTCTGTATG ATACCCAGAA AGTAATCAAG CGTGCAGAAG
 L  V  L  F  S  M  F  L  L  Y  D  T  Q  K  V  I  K  R  A  E>

970        980        990       1000       1010       1020
TATCACCAAT GTATGGAGTT CAAAAATATG ATCCCATTAA CTCGATGCTG AGTATCTACA
 V  S  P  M  Y  G  V  Q  K  Y  D  P  I  N  S  M  L  S  I  Y>

1030       1040       1050       1060       1070       1080
TGGATACATT AAATATATTT ATGCGAGTTG CAACTATGCT GGCAACTGGA GGCAACAGAA
 M  D  T  L  N  I  F  M  R  V  A  T  M  L  A  T  G  G  N  R>

1090       1100       1110       1120       1130       1140
AGAAATGAAG TGACTCAGCT TCTGGCTTCT CTGCTACATC AAATATCTTG TTTAATGGGG
 K  K>

1150       1160       1170       1180       1190       1200
CAGATATGCA TTAAATAGTT TGTACAAGCA GCTTTCGTTG AAGTTTAGAA GATAAGAAAC 1210       1220       1230       1240       1250       1260
ATGTCATCAT ATTTAAATGT TCCGGTAATG TGATGCCTCA GGTCTGCCTT TTTTTCTGGA 1270       1280       1290       1300       1310
GAATAAATGC AGTAATCCTC TCCCAAATAA GCACACACAA AAAAAAAAAA AAAAAA
```

FIG.2B

Sequence of SCM3

```
         10         20         30         40         50         60
GTGGAGATGT ATGCAGCATA CAGCAGCCGC TAGTTTTCCT CAGCTTCACA TCCTGGGTGT 70         80         90        100        110        120
CGGGGGGCTG CCACCTTGAT CATGGGAGTG CCCAGTGTAG TCAGTGCCAT ACCTATCAGG
                      M   G   V   P   S   V   V   S   A   I   P   I   R>

130        140        150        160        170        180
GCAGATTGTT CCTCCAAACC CCAGCCCCTC CTGCAGGGCC AGCCTCACCT CTACTTTTCC
A   D   C   S   K   P   Q   P   L   L   Q   G   Q   P   H   L   Y   F   S>

190        200        210        220        230        240
CCTAAGCTTT TGTGCCAGCT CCGGGGTTCC TTCTTGCCTG TCCACTCAGC CTGCCCTGGT
P   K   L   L   C   Q   L   R   G   S   F   L   P   V   H   S   A   C   P   G>

250        260        270        280        290        300
CCTCTCCTAA CCAGGATGCC CCAGGCAACC ACTGTTTCTC TGCCTTTAGG TTCCTGGAGT
P   L   L   T   R   M   P   Q   A   T   T   V   S   L   P   L   G   S   W   S>

310        320        330        340        350        360
TTGACAGAGG ATAGAGATGT TTCTGGAGAA TGGCCACGAG CTTTCCCAGA TACCCCACCT
L   T   E   D   R   D   V   S   G   E   W   P   R   A   F   P   D   T   P   P>

370        380        390        400        410        420
GGGATGACTA CTAGCGTCTT CCCTGTTGCC GGTGCCTGCC ACAGTGTAAA AAGCCTGCAG
G   M   T   T   S   V   F   P   V   A   G   A   C   H   S   V   K   S   L   Q>

430        440        450        460        470        480
AGACAACGGG GTGCCTCCCC ATCTCGGGAG AGAAAACCCA CGGGGGTGTC GGTGATCTAC
R   Q   R   G   A   S   P   S   R   E   R   K   P   T   G   V   S   V   I   Y>

490        500        510        520        530        540
TGGGAGAGGC TCCTGCTAGG CTCAGGCAGT GGGCAAGCCA GCGTCAGCCT GCGACTGACC
W   E   R   L   L   G   S   G   S   G   Q   A   S   V   S   L   R   L   T>

550        560        570        580        590        600
TCCCCGCTTA GGCCTCCCGA GGGCGTCCGG CTTAGGGAAA AGACACTCAC AGAGCATGCG
S   P   L   R   P   P   E   G   V   R   L   R   E   K   T   L   T   E   H   A>

610        620        630        640        650        660
TTGCTGGGGA GGCAGCCCAG GACGCCTGAG CGGCAGAAAC CATGTGCACA GGAGGTCCCT
L   L   G   R   Q   P   R   T   P   E   R   Q   K   P   C   A   Q   E   V   P>

670        680        690        700        710        720
GGGAGAACCT TTGGGAGCGC CCAGGACCTG GAGGCTGCCG GCGGTCGGGG ACATCACCGA
G   R   T   F   G   S   A   Q   D   L   E   A   A   G   R   G   H   H   R>
```

FIG.4A

```
      730        740        750        760        770        780
ATGGGTGCAG TTTGGCAGGA GCCTCATAGA CTCCTCGGTG GCCAGGAGCC CTCGACCTGG
 M  G  A  V  W  Q  E  P  H  R  L  L  G  G  Q  E  P  S  T  W>

790        800        810        820        830        840
GACGAGCTGG GCGAGGCTCT TCACGCTGGG GAGAAGTCCT TCGAATGCAG GGCGTGCAGC
 D  E  L  G  E  A  L  H  A  G  E  K  S  F  E  C  R  A  C  S>

850        860        870        880        890        900
AAAGTGTTCG TGAAGAGCTC CGACCTCCTC AAGCACCTAC GCACCCACAC CGGGGAGCGG
 K  V  F  V  K  S  S  D  L  L  K  H  L  R  T  H  T  G  E  R>

910        920        930        940        950        960
CCCTACGAGT GCGCCCAGTG CGGCAAGGCC TTCAGCCAGA CGTCGCACTT GACGCAGCAC
 P  Y  E  C  A  Q  C  G  K  A  F  S  Q  T  S  H  L  T  Q  H>

970        980        990       1000       1010       1020
CAGCGCATCC ACAGCGGCGA GACGCCCTAC GCGTGCCCCG TGTGCGGCAA GGCCTTCCGG
 Q  R  I  H  S  G  E  T  P  Y  A  C  P  V  C  G  K  A  F  R>

1030       1040       1050       1060       1070       1080
CATAGCTCCT CGCTGGTGCG GCACCAGCGC ATCCACACGG CCGAGAAGTC CTTCCGCTGC
 H  S  S  S  L  V  R  H  Q  R  I  H  T  A  E  K  S  F  R  C>

1090       1100       1110       1120       1130       1140
TCCGAGTGCG GCAAGGCCTT CAGCCACGGC TCCAACCTCA GCCAGCACCG CAAGATCCAC
 S  E  C  G  K  A  F  S  H  G  S  N  L  S  Q  H  R  K  I  H>

1150       1160       1170       1180       1190       1200
GCGGGTGGGC GTCCTTATGC TTGCGCACAG TGTGGCCGCC GCTTCTGCCG CAACTCGCAC
 A  G  G  R  P  Y  A  C  A  Q  C  G  R  R  F  C  R  N  S  H>

1210       1220       1230       1240       1250       1260
CTGATCCAGC ACGAGCGTAC GCACACAGGC GAGAAGCCCT TCGTGTGCGC GCTCTGCGGT
 L  I  Q  H  E  R  T  H  T  G  E  K  P  F  V  C  A  L  C  G>

1270       1280       1290       1300       1310       1320
GCTGCCTTCA GCCAGGGCTC CTCGCTCTTT AAGCACCAGC GCGTGCACAC AGGCGAGAAG
 A  A  F  S  Q  G  S  S  L  F  K  H  Q  R  V  H  T  G  E  K>

1330       1340       1350       1360       1370       1380
CCCTTCGCCT GCCCACAGTG CGGCCGCGCC TTTAGCCACA GCTCCAACCT CACCCAGCAC
 P  F  A  C  P  Q  C  G  R  A  F  S  H  S  S  N  L  T  Q  H>

1390       1400       1410       1420       1430       1440
CAGCTCCTGC ACACGGGCGA GCGGCCCTTC CGCTGCGTGG ACTGTGGCAA GGCCTTCGCC
 Q  L  L  H  T  G  E  R  P  F  R  C  V  D  C  G  K  A  F  A>
```

FIG.4B

```
      1450        1460        1470        1480        1490        1500
AAGGGCGCCG  TGCTGCTCAG  CCACCGGCGC  ATTCACACGG  GCGAGAAGCC  CTTCGTGTGT
 K  G  A  V   L  L  S    H  R  R    I  H  T  G   E  K  P     F  V  C>

1510        1520        1530        1540        1550        1560
ACGCAGTGTG  GCCGCGCCTT  CCGTGAGCGC  CCGGCCCTCT  TCCACCACCA  GAGGATCCAT
 T  Q  C  G   R  A  F    R  E  R    P  A  L  F    H  H  Q    R  I  H>

1570        1580        1590        1600        1610        1620
ACCGGCGAGA  AGACCGTCCG  GCGATCCAGG  GCCAGCCTGC  ACCCCCAGGC  CAGGTCTGTT
 T  G  E  K   T  V  R    R  S  R    A  S  L  H    P  Q  A    R  S  V>

1630        1640        1650        1660        1670        1680
GCCGGGGCAT  CATCAGAAGG  TGCGCCAGCG  AAGGAAACCG  AGCCCACTCC  CGCCTCGGGC
 A  G  A  S   S  E  G    A  P  A    K  E  T  E    P  T  P    A  S  G>

1690        1700        1710        1720        1730        1740
CCAGCCGCCG  TCTCGCAGCC  AGCGGAGGTC  TGAGGTCACA  GGTTGCAGCC  CTGGCCTTCT
 P  A  A  V   S  Q  P    A  E  V>

1750        1760        1770        1780        1790        1800
GTGAATCCCT  TCCACAGCTA  AAGGGCATAT  GTCCTCTGCA  GATCCCACAG  CAAGAAAAAG 1810        1820        1830        1840        1850        1860
TCCCGTGCTT  GCTAGTCAGG  GACAAGGAGG  CCCTTTGGCT  GTGATTTCAT  TTGCACGTGG 1870        1880        1890        1900        1910        1920
GACAGGATTT  GCCAGTTCAC  CCACAGATCA  CACCTCCATC  CCCAAAGAGG  TAGCACTGCA 1930        1940        1950        1960        1970        1980
GCAACATCAG  GGGGAGGACG  TGGTGGCTGA  ACTCTAGTGG  GGCCGAGACT  ATTCAGAGCC 1990        2000        2010        2020        2030        2040
AGTAGGAGGC  CGACAGTCAC  AGCACTGCAC  TGTGGTGCGG  CTTCATGTGA  TATGACAGTG 2050        2060        2070        2080        2090        2100
GATGCTAAGG  TGAGAGGGAT  GCAGGCATGG  GTTGGGGGTG  GCCCAGAGAA  ACTTATGACA 2110        2120        2130        2140        2150        2160
GCTGTACACA  AACTGGCCGC  TGGAGAGATG  CCCGCTGAGG  GTATTCTCCC  CTCAACCCAC 2170        2180        2190        2200        2210        2220
TGCCTCTGTT  CATCCAAGAC  TTCCTAGGGG  CCAGCCTAGC  AGACAAGAGA  CCACAAGGGA 2230        2240        2250        2260        2270        2280
CTGGGGATCA  GGGTCTGGGC  TCTGTCAGCC  GCCACCTCTG  GGAAAGAGAA  AAGGTTTGGG
```

FIG.4C

```
      2290       2300       2310       2320       2330       2340
TCCACTGAAC ATCATGTTTG TAGACGCTGA CAGGTGGGGT CCTAATGAGA GCCAACAGAT 2350       2360       2370       2380       2390       2400
GCTCACTGCC AGCTCCTGTC CTGAGTACTG GGAAGTTTCT CCTGAAGCCC TGTGAGATGG 2410       2420       2430       2440       2450       2460
CTCTGTGGCT GGTATCCCGA CTTGGAAGAT GAGGAAACTG AGGCACACGG CCTGGCCTGG 2470       2480       2490       2500       2510       2520
CTTCACACAC ATAGCCGACT CAGGAGAGGG ATGCCCATGG GGGAACATGT GACTCTCAGC 2530       2540       2550       2560       2570       2580
ATTGGAAGGA CAGAGCTAGG ATGATGGCTT TCCGGTGGCA CTCGTTCAGG TTTTTGCCCA 2590       2600       2610       2620       2630       2640
AGTCTCAGCT TGGCCAAGGC CTGTCACTGA CTGGTTTACC AAAGTCGATG TGAGGAGGAG 2650       2660       2670       2680       2690       2700
GCTTTATACC TGAGGGGATG ATGTTAACTT CAGACAAGAT GGAGCTGCTC ACTTTTGCCG 2710       2720       2730       2740       2750       2760
GGTTTGGTGG CCACTTCACC CCCAACCCTG TCTCACCCCC ATTATCCCTC CTCAATTGGA 2770       2780       2790       2800       2810       2820
GGCTGGACAG AGCTGAATAG GAAAGACTTG CTATTGCCTA AGGCTATGTG TGACACCCTC 2830       2840       2850       2860       2870       2880
CTGAGGACCT CCCCACCCCA GTGTAATGGC CCTTCATGGC AGGGACAGAA AGGTGGACTG 2890       2900       2910       2920       2930       2940
GGGGCCATTT GCTTCCTGTG GCCTTCAGCA GACCAGGCCC TGTCCCTACC TGGAGCCTCA 2950       2960       2970       2980       2990
CCTCCAAGGA AATTCATGTT CTCCTTAATG GAAAAAAAAA AAAAAAAAA AA
```

FIG.4D

Features of SCM3 protein:

```
              10         20         30         40         50         60
       MGVPSVVSAI PIRADCSSKP QPLLQGQPHL YFSPKLLCQL RGSFLPVHSA CPGPLLTRMP

>MybDNA bind
              |
              70  |       80         90        100        110        120
       QATTVSLPLG SWSLTEDRDV SGEWPRAFPD TPPGMTTSVF PVAGACHSVK SLQRQRGASP 130        140        150        160        170        180
       SRERKPTGVS VIYWERLLLG SGSGQASVSL RLTSPLRPPE GVRLREKTLT EHALLGRQPR 190        200        210        220        230        240
       TPERQKPCAQ EVPGRTFGSA QDLEAAGGRG HHRMGAVWQE PHRLLGGQEP STWDELGEAL >ZINC1                              >ZINC1
             |                                  |
             250        260        270        |280        290        300
       HAGEKSFECR ACSKVFVKSS DLLKHLRTHT GERPYECAQC GKAFSQTSHL TQHQRIHSGE >ZINC1                              >ZINC1
             |                                  |
            |310        320        330        | 340        350        360
       TPYACPVCGK AFRHSSSLVR HQRIHTAEKS FRCSECGKAF SHGSNLSQHR KIHAGGRPYA >ZINC1                 >ZINC1                             >ZINC1
          |                       |                                 |
          |  370        380       390        400        410        |420
       CAQCGRRFCR NSHLIQHERT HTGEKPFVCA LCGAAFSQGS SLFKHQRVHT GEKPFACPQC >ZINC1                             >ZINC1
                                 |                                  |
             430        440     | 450        460        470        | 480
       GRAFSHSSNL TQHQLLHTGE RPFRCVDCGK AFAKGAVLLS HRRIHTGEKP FVCTQCGRAF 490        500        510        520        530        540
       RERPALFHHQ RIHTGEKTVR RSRASLHPQA RSVAGASSEG APAKETEPTP ASGPAAVSQP

AEV
```

FIG.5

Sequence of SCM113

```
          10         20         30         40         50         60
CTTGGAGTGA GTGGACGCAC TCGGGAATTG TAGGAGGACG AGGCTCAGCT CTTGCCAGGC 70         80         90        100        110        120
CAAATTGAGA CATGTCTGAC ACAAGCGAGA GTGGTGCAGG TCTAACTCGC TTCCAGGCTG
            M  S  D   T  S  E  S   G  A  G   L  T  R    F  Q  A>

130        140        150        160        170        180
AAGCTTCAGA AAAGGACAGT AGCTCGATGA TGCAGACTCT GTTGACAGTG ACCCAGAATG
 E  A  S  E   K  D  S   S  S  M   M  Q  T  L   L  T  V   T  Q  N>

190        200        210        220        230        240
TGGAGGTCCC AGAGACACCG AAGGCCTCAA AGGCACTGGA GGTCTCAGAG GATGTGAAGG
 V  E  V  P   E  T  P   K  A  S   K  A  L  E   V  S  E   D  V  K>

250        260        270        280        290        300
TCTCAAAAGC CTCTGGGGTC TCAAAGGCCA CAGAGGTCTC AAAGACCCCA GAGGCTCGGG
 V  S  K  A   S  G  V   S  K  A   T  E  V  S   K  T  P   E  A  R>

310        320        330        340        350        360
AGGCACCTGC CACCCAGGCC TCGTCTACTA CTCAGCTGAC TGATACCCAG GTTCTGGCAG
 E  A  P  A   T  Q  A   S  S  T   T  Q  L  T   D  T  Q   V  L  A>

370        380        390        400        410        420
CTGAAAACAA GAGTCTAGCA GCTGACACCA AGAAACAGAA TGCTGACCCG CAGGCTGTGA
 A  E  N  K   S  L  A   A  D  T   K  K  Q  N   A  D  P   Q  A  V>

430        440        450        460        470        480
CAATGCCTGC CACTGAGACC AAAAAGGTCA GCCATGTGGC TGATACGAAG GTCAATACAA
 T  M  P  A   T  E  T   K  K  V   S  H  V  A   D  T  K   V  N  T>

490        500        510        520        530        540
AGGCTCAGGA GACTGAGGCT GCACCCTCTC AGGCCCCAGC AGATGAACCT GAGCCTGAGA
 K  A  Q  E   T  E  A   A  P  S   Q  A  P  A   D  E  P   E  P  E>

550        560        570        580        590        600
GTGCAGCTGC CCAGTCTCAG GAGAATCAGG ATACTCGGCC CAAGGTCAAA GCCAAGAAAG
 S  A  A  A   Q  S  Q   E  N  Q   D  T  R  P   K  V  K   A  K  K>

610        620        630        640        650        660
CCCGAAAGGT GAAGCATCTG GATGGGGAAG AGGATGGCAG CAGTGATCAG AGTCAGGCTT
 A  R  K  V   K  H  L   D  G  E   E  D  G  S   S  D  Q   S  Q  A>

670        680        690        700        710        720
CTGGAACCAC AGGTGGCCGA AGGGTCTCAA AGGCTCTAAT GGCCTCAATG GCCCGCAGGG
 S  G  T  T   G  G  R   R  V  S   K  A  L  M   A  S  M   A  R  R>
```

FIG.6A

```
           730        740        750        760        770        780
CTTCAAGGGG TCCCATAGCC TTTTGGGCCC GCAGGGCATC AAGGACTCGG GTTGGCTGCT
  A  S  R  G   P  I  A   F  W  A   R  R  A  S   R  T  R   V  G  C>

790        800        810        820        830        840
TGGGCCCGGA GAGCCTTGCT CTCCTGAGAT CACCTAAAGC CCGTAGGGGC AAGGCTCGCC
  L  G  P  E   S  L  A   L  L  R   S  P  K  A   R  R  G   K  A  R>

850        860        870        880        890        900
GTAGAGCTGC CAAGCTCCAG TCATCCCAAG AGCCTGAAGC ACCACCACCT CGGGATGTGG
  R  R  A  A   K  L  Q   S  S  Q   E  P  E  A   P  P  P   R  D  V>

910        920        930        940        950        960
CCCTTTTGCA AGGGAGGGCA AATGATTTGG TGAAGTACCT TTTGGCTAAA GACCAGACGA
  A  L  L  Q   G  R  A   N  D  L   V  K  Y  L   L  A  K   D  Q  T>

970        980        990       1000       1010       1020
AGATTCCCAT CAAGCGCTCG GACATGCTGA AGGACATCAT CAAAGAATAC ACTGATGTGT
  K  I  P  I   K  R  S   D  M  L   K  D  I  I   K  E  Y   T  D  V>

1030       1040       1050       1060       1070       1080
ACCCCGAAAT CATTGAACGA GCAGGCTATT CTTTGGAGAA GGTATTTGGG ATTCAATTGA
  Y  P  E  I   I  E  R   A  G  Y   S  L  E  K   V  F  G   I  Q  L>

1090       1100       1110       1120       1130       1140
AGGAAATTGA TAAGAATGAC CACTTGTACA TTCTTCTCAG CACCTTAGAG CCCACTGATG
  K  E  I  D   K  N  D   H  L  Y   I  L  L  S   T  L  E   P  T  D>

1150       1160       1170       1180       1190       1200
CAGGCATACT GGGAACGACT AAGGACTCAC CCAAGCTGGG TCTGCTCATG GTGCTTCTTA
  A  G  I  L   G  T  T   K  D  S   P  K  L  G   L  L  M   V  L  L>

1210       1220       1230       1240       1250       1260
GCATCATCTT CATGAATGGA AATCGGTCCA GTGAGGCTGT CATCTGGGAG GTGCTGCGCA
  S  I  I  F   M  N  G   N  R  S   S  E  A  V   I  W  E   V  L  R>

1270       1280       1290       1300       1310       1320
AGTTGGGGCT GCGCCCTGGG ATACATCATT CACTCTTTGG GGACGTGAAG AAGCTCATCA
  K  L  G  L   R  P  G   I  H  H   S  L  F  G   D  V  K   K  L  I>

1330       1340       1350       1360       1370       1380
CTGATGAGGT TGTGAAGCAG AAGTACCTGG ACTATGCCAG AGTCCCCAAT AGCAATCCCC
  T  D  E  V   V  K  Q   K  Y  L   D  Y  A  R   V  P  N   S  N  P>

1390       1400       1410       1420       1430       1440
CTGAATATGA GTTCTTCTGG GGCCTGCGCT CTTACTATGA GACCAGCAAG ATGAAAGTCC
  P  E  Y  E   F  F  W   G  L  R   S  Y  Y  E   T  S  K   M  K  V>
```

FIG.6B

```
       1450       1460       1470       1480       1490       1500
TCAAGTTTGC CTGCAAGGTA CAAAAGAAGG ATCCCAAGGA ATGGGCAGCT CAGTACCGAG
  L K F A    C K V     Q K K     D P K E    W A A     Q Y R>

1510       1520       1530       1540       1550       1560
AGGCGATGGA AGCGGATTTG AAGGCTGCAG CTGAGGCTGC AGCTGAAGCC AAGGCTAGGG
  E A M E    A D L     K A A     A E A A    A E A     K A R>

1570       1580       1590       1600       1610       1620
CCGAGATTAG AGCTCGAATG GGCATTGGGC TCGGCTCGGA GAATGCTGCC GGGCCCTGCA
  A E I R    A R M     G I G     L G S E    N A A     G P C>

1630       1640       1650       1660       1670       1680
ACTGGGACGA AGCTGATATC GGACCCTGGG CCAAAGCCCG GATCCAGGCG GGAGCAGAAG
  N W D E    A D I     G P W     A K A R    I Q A     G A E>

1690       1700       1710       1720       1730       1740
CTAAAGCCAA AGCCCAAGAG AGTGGCAGTG CCAGCACTGG TGCCAGTACC AGTACCAATA
  A K A K    A Q E     S G S     A S T G    A S T     S T N>

1750       1760       1770       1780       1790       1800
ACAGTGCCAG TGCCAGTGCC AGCACCAGTG GTGGCTTCAG TGCTGGTGCC AGCCTGACCG
  N S A S    A S A     S T S     G G F S    A G A     S L T>

1810       1820       1830       1840       1850       1860
CCACTCTCAC ATTTGGGCTC TTCGCTGGCC TTGGTGGAGC TGGTGCCAGC ACCAGTGGCA
  A T L T    F G L     F A G     L G G A    G A S     T S G>

1870       1880       1890       1900       1910       1920
GCTCTGGTGC CTGTGGTTTC TCCTACAAGT GAGATTTTAG ATATTGTTAA TCCTGCCAGT
  S S G A    C G F     S Y K>

1930       1940       1950       1960       1970       1980
CTTTCTCTTC AAGCCAGGGT GCATCCTCAG AAACCTACTC AACACAGCAC TCTAGGCAGC 1990       2000       2010       2020       2030       2040
CACTATCAAT CAATTGAAGT TGACACTCTG CATTAAATCT ATTTGCCAAA AAAAAAAAAA

AAAAAA
```

FIG.6C

GENES IN THE CONTROL OF HEMATOPOIESIS

This application claims benefit under 35 U.S.C. 119(e) of U.S. Provisional Application No. 60/155,232 filed Aug. 03, 1998 now abn.

FIELD OF THE INVENTION

The present invention relates to nucleic acid and amino acid sequences of three novel genes involved in the control of hematopoiesis.

BACKGROUND OF THE INVENTION

Hematopoiesis (used interchangeably with hemopoiesis) is a process whereby multi-potent stem cells give rise to lineage-restricted progeny. Hemopoietic stem cells (HSCs) are the only cells in the hematopoietic system that produce other stem cells and give rise to the entire range of blood and immune system cells. In humans, $CD34^+Thy-1^+Lin^-$ cells from bone marrow and mobilized peripheral blood are highly enriched for HSCs (Murray et al., Blood Cells, 20:354–370 (1995a); Murray et al., Blood, 85:368–378 (1995b)). This cell population is capable of self-renewal and long term multilineage differentiation and has been successfully used for autologous transplantation (Gazitt et al., Blood, 86:381–389 (1995)). Since HSCs self-renew and are multi-potent, they are ideal candidates for gene therapy. Gene therapy is a new treatment modality for a variety of genetic, neoplastic, or infectious diseases and has the potential to correct defects in all mature cells derived from HSC.

The molecular basis of hematopoiesis remains poorly understood. A greater understanding of the process whereby HSCs give rise to lineage-restricted progeny would facilitate the exploitation of HSCs for transplantation and gene therapy. To achieve this, the molecular pathways controlling hemopoietic cell growth and differentiation have been investigated. To this end, the present invention concerns the identification of candidate HSC regulatory genes and their impact on hematopoiesis.

In the present invention, a cDNA library has been built and characterized from human $CD34^+Thy-1^+$ stem cells. Sequence analysis of the cDNA library revealed a high degree of novel proteins which may play a role in hematopoiesis. To enrich for candidate hemopoietic stem cell (HSC) regulatory genes, RNA expression profiling was performed and cDNAs whose expression was enriched in HSC were selected and compared to other differentiated blood cell types. Candidate genes were fully sequenced. The HSC-enriched genes which encode full length novel gene products were subcloned into a retroviral expression vector, which was used to overexpress the gene product in freshly isolated HSCs. Three novel HSC regulatory genes and the proteins which they encode were identified. Each of the novel cDNAs are enriched in HSCs compared to their differentiated progeny, and when overexpressed in HSCs blocks the differentiation of stem cells.

SUMMARY OF THE INVENTION

The present invention discloses three novel genes involved in HSC regulation, hereinafter referred to as SCM 26, SCM 3, and SCM 113.

In a first embodiment, the invention concerns isolated polynucleotide sequences encoding a polypeptide comprising an amino acid sequence selected from the group consisting of the amino acid sequence of SEQ ID NO. 2; the amino acid sequence of SEQ ID NO. 4; the amino acid sequence of residues 1–239 of SEQ ID NO.4; the amino acid sequence of residues 240–543 of SEQ ID NO. 4; the amino acid sequence of SEQ ID NO. 6; and an amino acid sequence functionally equivalent to the above enumerated sequences.

In a second embodiment, the invention relates to an isolated DNA sequence comprising a nucleotide sequence selected from the group consisting of the polynucleotide sequence of SEQ ID NO 1; the polynucleotide sequence of SEQ ID NO. 3; the polynucleotide sequence of SEQ ID NO. 5; and a polynucleotide sequence at least 85% identical to a polynucleotide sequence as disclosed above. In one aspect, the isolated polynucleotide sequence may consist of the complement of the polynucleotide sequences of those listed above.

In a third embodiment, the invention concerns, an isolated polypeptide comprising a member selected from the group consisting of, a polypeptide comprising the amino acid sequence of SEQ ID NO. 2; a polypeptide comprising the amino acid residues 26–40 of SEQ ID NO. 2; a polypeptide comprising the amino acid residues 25–82 of SEQ ID NO. 2; a polypeptide comprising the amino acid residues 147–157 of SEQ ID NO. 2; a polypeptide comprising the amino acid residues 266–275 of SEQ ID NO. 2; a polypeptide comprising the amino acid sequence of SEQ ID NO. 4; a polypeptide comprising the amino acid residues 1–239 of SEQ ID NO. 4; a polypeptide comprising the amino acid residues 240–543 of SEQ ID NO. 4; a polypeptide comprising the amino acid sequence of SEQ ID NO. 6; or a polypeptide having at least 85% identity to said polypeptides disclosed above. In a preferred aspect, the isolated polypeptide comprises the amino acid sequence of SEQ ID Nos. 2, 4, 6, or a polypeptide having an amino acid sequence with 95% identity thereto. In another aspect, the invention relates to an isolated polypeptide comprising a member selected from the group consisting of the amino acid residues 26–40 of SEQ ID NO. 2; the amino acid residues 25–82 of SEQ ID NO. 2; the amino acid residues 147–157 of SEQ ID NO. 2; the amino acid residues 266–275 of SEQ ID NO. 2; and a polypeptide having at least 97% identity thereto. In yet a further aspect, the invention relates to a DNA sequence encoding one of the above enumerated polypeptides.

In a fourth embodiment, the invention concerns a vector which incorporates one of the claimed polynucleotide sequences of the invention. In a preferred aspect, the vector is a retroviral vector, adenoviral vector, or adeno-associated vector. In a further preferred aspect, a host cell is claimed which includes the vector. A preferred host cell is a hematopoietic cell, particularly a human $CD34^+$ cell.

In a fifth embodiment, the invention concerns a method of increasing the effective dose of hematopoietic stem cells in a mammalian subject, comprising obtaining a population of $CD34^+$ cells which includes a subpopulation of hematopoietic stem cells; introducing into the $CD34^+$ cells a polynucleotide sequence of the invention encoding a disclosed polypeptide of the invention; obtaining a subpopulation of genetically modified stem cells which overexpress said polypeptide; and administering said subpopulation of genetically modified cells to a subject wherein the effective dose of the hematopoietic stem cells is increased. In a further aspect, the invention includes the step of selecting hematopoietic stem cells either prior to or after genetic modification. In yet another aspect, the invention includes the step of culturing the population of hematopoietic $CD34^+$ cells either prior to or after genetic modification.

In a sixth embodiment the invention concerns, a method of increasing the effective dose of gene modified cells comprising obtaining a population of hematopoietic CD34+ cells which includes a subpopulation of hematopoietic stem cells; introducing into the population of CD34+ cells a polynucleotide sequence of the invention; introducing into the population of CD34+ cells a second polynucleotide sequence wherein said second polynucleotide sequence encodes a therapeutic gene; obtaining genetically modified cells wherein said cells are capable of expressing the polynucleotide sequence of the invention and the therapeutic gene wherein the effective dose of the cells capable of expressing the therapeutic gene is increased compared to wild-type cells; and administering the genetically modified cells to a mammalian subject.

In an seventh embodiment, the invention concerns a method of blocking the differentiation of mammalian hematopoietic stem cells in vitro comprising the steps of; isolating CD34+ cells from a source of hematopoietic cells; introducing a vector comprising the claimed polynucleotide sequences into the CD34+ cells, whereby a population of said cells are genetically modified by said vector; culturing the modified CD34+ cells in the presence of at least one cytokine in an amount sufficient to support growth of the modified cells; and selecting cells in which the polypeptide is overexpressed whereby differentiation is blocked. In a preferred aspect, the mammalian hematopoietic cells are human. In another preferred aspect, the CD34+ cells are further selected based on the following phenotypes Thy-1+, CD34+Thy-1+, CD34+Thy-1+Lin−, or CD34+Thy-1+CD38−, either prior to or after introduction of the vector. In a preferred aspect, the method of blocking differentiation of mammalian hematopoietic stem cells includes introducing a vector comprising a claimed polynucleotide sequence into CD34+ cells, genetically modifying a population of said cells with said sequence; allowing the expression of the polynucleotide sequence in said cells and blocking differentiation. The method may be in vitro or in vivo.

In an eighth embodiment, the invention concerns, a method of producing a polypeptide of the invention comprising the steps of: culturing a host cell comprising a polynucleotide sequence encoding the claimed polypeptides under conditions suitable for the expression of the polypeptide, and recovering said polypeptide from the host culture.

In an ninth embodiment, the invention relates to an antibody which binds to the claimed polypeptides. Additionally, the invention concerns a method of identifying mammalian hematopoietic stem cells or progeny thereof comprising, preparing an antibody to a claimed polypeptide; purifying the antibody; exposing the a population of the mammalian hematopoietic cells to the antibody; allowing said cells to bind to the antibody; and selecting said bound cells.

All publications and patent applications mentioned in this specification are indicative of the level of skill of those skilled in the art to which this invention pertains. All publications and patent applications cited herein are hereby incorporated by reference in their entirety. Throughout this specification, the singular form "a", "an", and "the" include plural references unless the context clearly dictates otherwise.

Other objects, features, advantages and aspects of the present invention will become apparent to those skilled in the art from the following description. It should be understood however, that the following description and the specific examples, while indicating preferred embodiments of the invention are given by way of illustration only. Various changes and modifications within the spirit and scope of the disclosed invention will become readily apparent to those skilled in the art from reading the disclosure.

BRIEF DESCRIPTION OF THE DRAWINGS

The following figures depict certain embodiments of the invention. They are illustrative only and do not limit the invention otherwise disclosed herein.

FIG. 2 illustrates the nucleotide sequence and predicted amino acid sequence of SCM 26 and corresponds to SEQ ID NO. 1. The cDNA insert in clone SCM 26 is 1316 nucleotides in length and includes a polyA+ tail of 18 residues. There is a single long open reading frame of 345 amino acids starting from the first in frame methionine at position 51 and ending with a TGA stop codon at position 1086. SCM 26 encodes a putative signal peptide sequence and seven transmembrane domains giving a cell surface location with an extracellular amino terminus and an intracellular COOH terminus as represented in FIG. 3. The northern blot analysis indicates two SCM 26 transcripts. One transcript is 1.5 Kb, and the second transcript is 2.4 Kb. The cDNA clone as sequenced herein corresponds to the smaller transcript, however, the invention also relates to the polynucleotide sequence encoding a polypeptide of the 2.4 Kb transcript.

FIG. 3A illustrates a hydrophobicity plot of SCM 26 and the predicted signal peptide and 7 transmembrane regions. FIG. 3B shows the predicted topology of the SCM 26 protein in the membrane. FIG. 3C illustrates that the SCM 26 protein is enriched in CD34+ cells.

FIG. 4 illustrates the nucleotide sequence of SCM 3 and corresponds to SEQ ID NO. 3. The SCM 3 cDNA contains 2990 nucleotides and ends in a ploy A tail. The predicted open reading frame begins at nucleotide 82 and ends at nucleotide 1710 and encodes a protein of 543 amino acids.

FIG. 5 illustrates specific features of the SCM 3 protein (SEQ ID NO. 4. The protein contains a region predicted to bind the myb factor at amino acid 72 and 9 predicted zinc-finger regions of the C2-H2 family.

FIG. 6 illustrates the nucleotide and amino acid sequence of SCM 113 having 2027 nucleotides with an open reading frame from nucleotide 72 to 1889 and encoding a predicted protein of 607 amino acids (SEQ ID NO. 5).

DETAILED DESCRIPTION OF THE INVENTION

Figure 1:
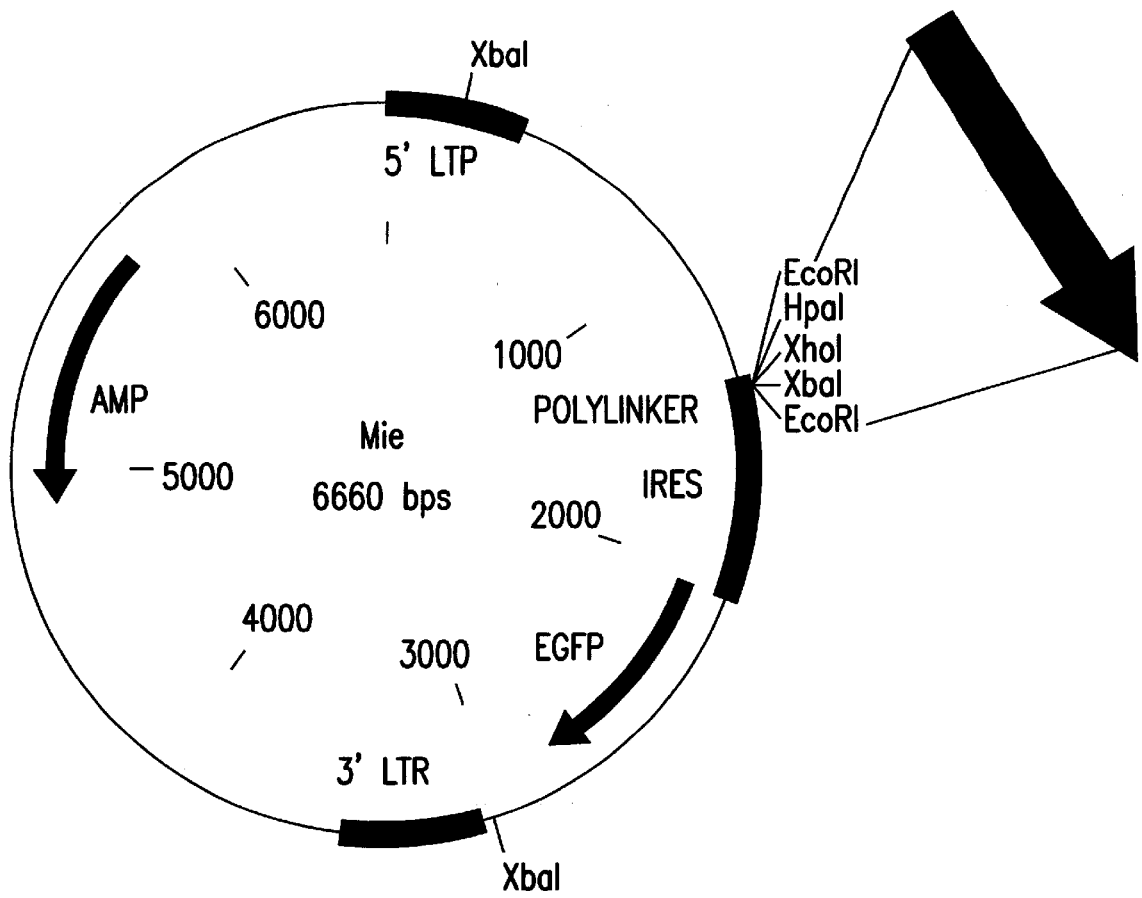
FIG. 1 illustrates the MIE vector. cDNAs (large arrow) are inserted into the polylinker. Transcription is driven from the 5'LTR. EGFP is included as a selective marker.

Three novel cDNAs were found to be enriched in hematopoietic stem cells (HSCs). These novel genes are disclosed as SCM 26, SCM 3 and SCM 116 and are illustrated in FIGS. 2, 4 and 6, respectively. The term "gene" are used herein means the segment of DNA involved in producing a polypeptide chain; it includes regions preceding and following the coding region (leader and trailer) as well as intervening sequences (introns) between individual coding segments (exons).

The invention includes an isolated polynucleotide encoding a polypeptide having the amino acid sequence as depicted in SEQ ID NO. 2, SEQ ID NO. 4, SEQ ID NO. 6, the amino acid sequence of residues 1–239 of SEQ ID NO. 4, the amino acid sequence of residues 240–543 of SEQ ID NO. 4, and amino acid sequences functionally equivalent thereto.

The term "isolated" refers to molecules, either nucleic acids or amino acid sequences, that are removed from or separated from their original environment and are at least 60% free, preferably 75% free, more preferably 90% free and most preferably 95% free from other components with which they are naturally associated. Preferably the polypeptides and polynucleotides of the invention are purified to homogeneity.

"Nucleic acid sequence" refers to an oligonucleotide, nucleotide or polynucleotide, and fragments or portions thereof, and to DNA or RNA of genomic or synthetic origin and include sense or antisense strands. A DNA "coding sequence of" or a "nucleotide sequence encoding" a particular protein, is a DNA sequence which is transcribed and translated into a protein when placed under the control of appropriate regulatory sequences. The term "polypeptide" is used interchangeably herein with the term protein.

The term "functional equivalent" is used in connection with a protein, the sequence of which is dictated by at least a part of the DNA sequences depicted in FIG. 2, 4 or 6. The term means a protein having a like function and like or improved specific activity, and a similar amino acid sequence. "Similarity" or "identity" between two polypeptides or polynucleotides is determined by comparing the amino acid sequence and conserved amino acid substitutes of one polypeptide to the sequence of a second polypeptide. Similarity may be determined by procedures well known in the art, for example a BLAST program (Basic Local Alignment Search Tool at the National Center for Biological Information). The present invention includes polypeptides having an amino acid sequence which is at least 75% identical to the polypeptides of SEQ ID NOs. 2, 4, 6 or fragments thereof. It is preferred that the degree of identity is at least 85%, even more preferably at least 90%, most preferably is least 95%, still more preferably at least 97%, and most preferably at least 99% identical to a protein depicted in SEQ ID NOs. 2, 4, 6 or fragments thereof.

"Identity" as the term is used herein, refers to a polynucleotide or polypeptide sequence comprising a percentage of the same bases as a reference polynucleotide or polypeptide. For example, a polynucleotide or polypeptide which is at least 90% identical to a reference polynucleotide or polypeptide, has polynucleotide bases or amino acid residues which are identical in 90% of the bases or residues which make up the reference polynucleotide or polypeptide and may have different bases or residues in 10% of the bases or residues which comprise that polynucleotide or polypeptide sequence.

The term "fragment" when used in connection with an amino acid sequence means a part of the sequence depicted in FIG. 2, 5 or 6 and having at least 10 amino acid residues, preferably 50 amino acids residues, even more preferably 100 amino acid residues and most preferably 200 amino acid residues which are similar to the amino acid sequences of FIG. 2, 5 or 6.

A variant, i.e. a fragment polypeptide and reference polypeptide may differ in amino acid sequence by one or more substitutions, additions, deletions, truncations which may be present in any combination. Among preferred variants are those that vary from a reference polypeptide by conservative amino acid substitutions. Such substitutions are those that substitute a given amino acid by another amino acid of like characters. The following non-limiting list of amino acids are considered conservative replacements (similar): a) alanine, serine, and threonine; b) glutamic acid and asparatic acid; c) asparagine and glutamine d) arginine and lysine; e) isoleucine, leucine, methionine and valine and f) phenylalaine, tyrosine and tryptophan. Most highly preferred are variants which retain the same biological function and activity as the reference polypeptide from which it varies.

The invention includes degenerate polynucleotides, DNA sequences which encode the polypeptides of the invention and particularly the amino acid sequence of SEQ ID NOs. 2, 4, 6 and fragments thereof, but having variations in the nucleotide coding sequences. As well known in the art, the degeneracy of the genetic code allows for various nucleic acid sequences, DNA's and RNA's, to encode the same protein. In most cases an amino acid is encoded by two or more synonymous codons, for example the amino acid alanine is encoded by GCU, GCC and GCA. The invention includes polynucleotides encoding a variant of the polypeptide as shown in FIG. 2, FIG. 5 or FIG. 6. Such nucleotide variants are alternate forms of the polynucleotide sequence which may have a deletion, substitution, or addition of one or more nucleotides and which are functionally equivalent to the encoded protein.

An SCM gene as broadly used herein refers to the amino acid sequence of substantially purified SCM peptides obtained from any species, particularly preferred are mammalian, including human, mouse, and chicken, and most particularly human, and from any source whether natural, synthetic or recombinant. The term SCM expression is broadly used in this disclosure to mean the expression of a polynucleotide sequence of the invention. The polypeptides so expressed are referred to as SCM proteins.

The invention further includes an isolated DNA sequence including the polynucleotide sequence of SEQ ID NO. 1, SEQ ID NO. 3, SEQ ID NO. 5, a fragment thereof and a sequence having at least 85% identity thereto. Isolated nucleic acid sequences are substantially similar if they are capable of hybridizing under stringent conditions to the sequence of FIG. 2, 4 or 6. Isolated nucleic acid sequences are also considered substantially similar if they are polynucleotides which are at least 85%, preferably at least 90%, more preferably at least 95%, even more preferably 97%, and most preferably 99% identical to the sequences of SEQ ID NOs. 1, 3, 5 or a fragment thereof. In a preferred embodiment the fragment includes the polynucleotide encoding the amino acid sequence of residue 1–239 of SEQ ID NO. 4, variants and complementary sequences thereto. In another preferred embodiment the fragment includes the polynucleotide encoding the amino acid sequence of residue 240–543 of SEQ ID NO. 4., variants and complementary sequences thereto.

Where the term "fragment" is used with a nucleotide sequence, the term means a nucleotide sequence including part of the sequence depicted in FIG. 2, 4 or 6 and comprising as few as at least 30, 50, 75, 80, 100 or more nucleotides, preferably at least 200, 300, 400, 500, 600, or more nucleotides, even more preferably at least 800, 1000, 1500, 2000 or more nucleotides. Specifically with reference to a fragment of the nucleotide sequence of FIG. 2 (SCM 26), the fragment will have at least 100 nucleotides, preferably 500 nucleotides, even more preferably 800 nucleotides and most preferably at least 1000 nucleotides. Specifically with reference to a fragment of the nucleotide sequence of FIG. 4 (SCM 3), the fragment will have at least 1500 nucleotides, preferably 2000 nucleotides, and most preferably at least 2500 nucleotides. Specifically with reference to a fragment of the nucleotide sequence of FIG. 6 (SCM 113), the fragment will have at least 1000 nucleotides, preferably 1500 nucleotides, and most preferably at least 2000 nucleotides.

The invention further provides an isolated polynucleotide consisting of the complement of the above disclosed polynucleotides. The term complement refers to the binding of polynucleotides under permissive conditions by base pairing, for example the sequence of "AGT" binds to the complementary sequence "TCA". Most preferably a polynucleotide sequence will hybridized with the reference sequence i.e. SEQ ID NOs. 1, 3, or 6 or a part thereof under stringent hybridization conditions. Stringent hybridization conditions are those in which hybridization is effected between 50° and 60° C. in saline buffer solution. The DNA to be used for hybridization may be prepared in a conventional manner and be targeted to form an identifiable probe by procedures well known in the art.

The term antisense means nucleotide sequences that are complementary to a specific DNA or RNA sequence (sense strand). This invention further includes complementary or antisense polynucleotides.

The invention concerns isolated polypeptides which have the deduced the amino acid sequence selected from the group of SEQ ID NO. 2, SEQ ID NO. 4, SEQ ID NO. 6, fragments thereof, functionally equivalent polypeptides thereto. In general, a polypeptide fragment may have a sequence which is at least 10 amino acids, preferably at least 50 amino acid, even more preferably at least 100 amino acids, and most preferably at least 200 amino acids which are identical to the polypeptide sequence of FIG. 2, 5, or 6.

Specific mention is made of the following preferred non-limiting polypeptide fragments; The polypeptide including amino acid residues 1–239 of SEQ ID NO. 4; the polypeptide including amino acid residues 240–543 of SEQ ID NO.4; the polypeptide including amino acid residues 26–40 of SEQ ID NO. 2; the polypeptide including amino acid residues 25–82 of SEQ ID NO. 2; the polypeptide including amino acid residues 147–157 of SEQ ID NO. 2; and the polypeptide including amino acid residues 266–275 of SEQ ID NO. 2.

A functionally equivalent polypeptide of FIG. 2, 5 or 6 is a variant wherein one in which one or more amino acid residues are substituted with conserved or non-conserved amino acid residues, or one in which one or more amino acid residues includes a substituent group. Conservative substitutions are the replacements, one for another, among the aliphatic amino acids Ala, Val, Leu and Ile; interchange of the hydroxl residues Ser and Thr; exchange of the acidic residues Asp and Glu; substitution between amide residues Asn and Gln; exchange of the basic residues Lys and Arg; and replacements among aromatic residues Phe and Tyr.

In addition, the invention features polypeptide sequences having at least 75% identity with the polypeptide sequences illustrated in FIGS. 2, 5, 6, or fragments and functionally equivalent polypeptides thereof. In one embodiment, the polypeptides have at least 85% identity, more preferably at least 90% identity, even more preferably at least 95% identity, still more preferably at least 97% identity, and most preferably at least 99% identity with the amino acid sequences illustrated in FIGS. 2, 5, 6, or the fragments including amino acid residue 1–239 or 240–543 of FIG. 5.

While the SCM encoding sequence may be introduced as a construct into a host cell, in a preferred embodiment the SCM encoding sequence will be placed into a vector. The term "vector" means an agent used to carry new genes or DNA segments into cells. Vectors include the necessary elements for the transcription and translation of the inserted coding sequence. Preferred polynucleotides included in the construct or the vector are the sequences encoding for SCM 3, SCM 26, SCM 113 and functionally equivalent sequences having at least 85% identity thereto, and preferably having at least 90% identity thereto. Methods used to construct vectors are known and described in various publications. In particular techniques for constructing suitable vectors are reviewed in considerable detail in Sambrook et al., Molecular Cloning: A Laboratory Manual, $2^{nd}$ Ed., Cold Spring Harbor Laboratory Press, Cold Spring Harbor, N.Y. (1989).

Vectors may include but are not limited to viral vectors, such as baculovirus, retroviruses, adenoviruses, adeno-associated viruses, and herpes simplex viruses; bacteriophages; cosmids; plasmid vectors; synthetic vectors; and other recombination vehicles typically used in the art. In a preferred embodiment, the vector comprises a polynucleotide operatively linked to a regulatory sequence. Regulatory sequences include promoters, enhancers, polyadenylation signals, and other expression control elements. The promoter may be either a prokaryotic or eukaryotic promoter. The vector may further comprise a polyadenylation signal that is positioned 3' of the carboxy-terminal amino acid. Vectors containing both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). Specific examples include, pSG, pSV2CAT, pXt1 from Stratagene and pMSG, pSVL, pBPV and pSVK3 from Pharmacia. In order to optimize expression and/or in vitro transcription, it may be necessary to remove, add or alter 5' and/or 3' untranslated portions of the clones to eliminate potentially extra inappropriate alternative translation initiation codons or other sequences that may interfere with or reduce expression, either at the level of transcription or translation. Alternatively consensus ribosome binding sites can be inserted immediately '5' of the start codon to enhance expression. Both inducible regulatory systems and constitutive regulatory sequences are known in the art to function in various cell types.

Preferred vectors include retroviral vectors (See, Coffin et al., "Retroviruses", (1997) Chapter 9 pp; 437–473 Cold Springs Harbor Laboratory Press). Vectors useful in the invention are produced recombinantly by procedures already taught in the art. WO94/29438, WO97/21824 and WO97/21825 describe the construction of retroviral packaging plasmids and packing cell lines. Exemplary vectors include the pCMV mammalian expression vectors, such as pCMV6b and pCMV6c (Chiron Corp.), pSFFV-Neo, and pBluescript-Sk+. Non-limiting examples of useful retroviral vectors are those derived from murine, avian or primate retroviruses. Common retroviruses are those based on the Moloney murine leukemia virus (MoMLV-vector). Other MoMLV derived vectors include, Lmily, LINGFER, MINGFR and MINT (Chang et al., *Blood* 92:1–11 (1998)). Further vectors include those based on Gibbon ape leukemia virus (GALV) and Moloney murine sacroma virus (MoMSV) and spleen focus forming virus (SFFV). Vectors derived from the murine stem cell virus (MESV) include MESV-MiLy (Agarwal et al., *J. of Virology*, 72:3720–3728, (1998)). Retroviral vectors also include vectors based on lentiviruses, and non-limiting examples include vectors based on human immunodeficiency virus (HIV-1 and HIV-2). New vector systems are continually being developed to take advantage of particular properties of parent retroviruses such as host range, usage of alternative cell surface receptors and the like. The present invention is not limited to particular retroviral vectors, but may include any retroviral vector.

Particularly preferred vectors include DNA from a murine virus corresponding to two long terminal repeats, and a package signal. In one embodiment the murine viral vector is derived from a MoMLV or a MSCV.

In producing retroviral vector constructs, the viral gag, pol and env sequence will generally be removed from the virus, creating room for insertion of foreign DNA sequences. Genes encoded by foreign DNA are usually expressed under the control a strong viral promoter in the long terminal repeat (LTR). Selection of appropriate control regulatory sequences is dependent on the host cell used and selection is within the skill of one in the art. Numerous promoters are known in addition to the promoter of the LTR. Non-limiting examples include the phage lambda PL promoter, the human cytomegalovirus (CMV) immediate early promoter; the U3 region promoter of the Moloney Murine Sarcoma Virus (MMSV), Rous Sacroma Virus (RSV), or Spleen Focus Forming Virus (SFFV); Granzyme A promoter; Granzyme B promoter, CD34 promoter; and the CD8 promoter. Additionally inducible or multiple control elements may be used.

Such a construct can be packed into viral particles efficiently if the gag, pol and env functions are provided in trans by a packing cell line. Therefore when the vector construct is introduced into the packaging cell, the gag-pol and env proteins produced by the cell, assemble with the vector RNA to produce infectious virons that are secreted into the culture medium. The virus thus produced can infect and integrate into the DNA of the target cell, but does not produce infectious viral particles since it is lacking essential packaging sequences. Most of the packing cell lines currently in use have been transfected with separate plasmids, each containing one of the necessary coding sequences, so that multiple recombination events are necessary before a replication competent virus can be produced. Alternatively the packaging cell line harbors a provirus. (The DNA form of the reverse-transcribed RNA once its integrates into the genomic DNA of the infected cell). The provirus has been crippled so that although it may produce all the proteins required to assemble infectious viruses, its own RNA can not be packaged into virus. RNA produced from the recombinant virus is packaged instead. Therefore, the virus stock released from the packaging cells contains only recombinant virus. Non-limiting examples of retroviral packaging lines include PA12, PA317, PE501, PG13, ΨCRIP, RD114, GP7C-tTA-G10, ProPak-A (PPA-6), and PT67. Reference is made to Miller et al., *Mol. Cell Biol.* 6:2895 (1986); Miller et al., *Biotechniques* 7:980 (1989); Danos et al., *Proc. Natl. Acad. Sci.* USA 85:6460 (1988); Pear et al., *Proc. Natl. Acad. Sci.* USA 90:8392–8396 (1993); Rigg et al., *Virology* 218 (1996); and Finer et al., *Blood* 83:43–50 (1994).

Additionally preferred vectors include adenoviral vectors (See, Frey, B. M. et al., *Blood,* 91:2781, (1998); and WO 95/27071) and adeno-associated viral vectors (See, Chatterjee et al., Current Topics in Microbiol. And Immunol., 218:61–73, 1996). Also reference is made to Shenk, Chapter 6, 161–178, Breakefield et al., Chapter 8 201–235; Kroner-Lux et al., Chapter 9 235–256 in Stem cell Biology and Gene Therapy, eds. Quesenberry et al., John Wiley & Sons, 1998 and U.S. Pat. Nos. 5,693,531 and 5,691,176. The use of adenovirus-derived vectors may be advantageous under certain situation because they are not capable of infecting non-dividing cells, and unlike retroviral DNA, the adenoviral DNA is not integrated into the genome of the target cell. Further, the capacity to carry foreign DNA is much larger in adenoviral vectors than retroviral vectors. The adeno-associated viral vectors are another useful delivery system. The DNA of this virus may be integrated into non-dividing cells, and a number of polynucleotides have been successful introduced into different cell types using adeno-associated viral vectors.

In one embodiment, the construct or vector will include two or more heterologous nucleic acid sequences; a) the nucleic acid sequence encoding a polypeptide of the invention and b) one or more additional nucleic acid sequence. Preferably the additional nucleic acid sequence is a polynucleotide which encodes a selective marker, a structural gene, a therapeutic gene, a ribozyme, or an antisense sequence.

A selective marker may be included in the construct or vector for the purposes of monitoring successful genetic modification and for selection of cells into which DNA has been integrated. Non-limiting examples include drug resistance markers, such as G148 or hygromycin. Additionally negative selection may be used, for example wherein the marker is the HSV-tk gene. This gene will make the cells sensitive to agents such as acyclovir and gancyclovir. Selection may also be made by using a cell surface marker, for example, to select overexpression of SCM by fluorescence activated cell sorting (FACS). The NeoR (neomycin/G148 resistance) gene is commonly used but any convenient marker gene may be used whose gene sequences are not already present in the target cell can be used. Further non-limiting examples include low-affinity Nerve Growth Factor (NGFR), enhanced fluorescent green protein (EFGP), dihydrofolate reductase gene (DHFR) the bacterial hisD gene, murine CD24 (HSA), murine CD8a(lyt), bacterial genes which confer resistance to puromycin or phleomycin, and β-glactosidase.

In gene therapy cells are used which express heterologous genetic material in vivo. In the case of an in born genetic disease, the genetic material is suitably a gene for the normal protein. Additionally the gene may be for a protective protein or the gene may encode a protective RNA such as a ribozyme or antisense sequence. Gene Therapy may be in vivo, administering the vector to the subject so that host target cells are transformed in situ or ex vivo wherein the target cells are transformed in vitro and then introduced into the subject.

The structural gene may be the entire gene or only the functionally active fragment of the gene. The structural gene may include for example a gene that regulates cell differentiation or a therapeutic gene capable of compensating for a deficiency in a patient that arises from a defective endogenous gene. A therapeutic gene may be one that antagonizes production or function of an infectious agent, antagonizes pathological processes, improves a host's genetic makeup, or facilitates engraftment. Specific examples of a therapeutic gene or gene sequences are ones effective in the treatment of adenosine deaminase deficiency (ADA); sickle cell anemia; recombinase deficiency; recombinase regulatory gene deficiency; HIV such as an antisense or trans-dominant REV gene or a gene carrying a herpes simplex virus thymidine kinase (HSV-tk)).

For human patients the therapeutic gene will generally be of human origin although genes of closely related species that exhibit high homology and biologically identical or equivalent function in humans may be used if the gene does not produce an adverse immune reaction in the recipient. The second polynucleotide sequence may encode new antigens or drug resistant genes or may encode a toxin or an apoptosis inducer effective to specifically kill cancerous cells, or a specific suicide gene to cancerous hematopoietic cells may be included.

A therapeutic active amount of a nucleic acid sequence or a therapeutic gene is an amount effective at dosages and for a period of time necessary to achieve the desired result. This amount may vary according to various factors including but not limited to sex, age, weight of a subject, and the like.

The additional polynucleotide sequence(s) may be introduced into the host cell on the same vector as the polynucleotide sequence encoding the polypeptides of the invention or the additional polynucleotide sequence may be introduced into the host cells on a second vector. In a preferred embodiment a selective marker will be included on the same vector as the SCM encoding nucleic acid sequence. In another embodiment, the vector will include at least three polynucleotide encoding sequences comprising the SCM encoding polynucleotide, a selectable marker and a therapeutic gene.

The host target cells of the present invention are mammalian cells and these include but are not limited to humans, mice, monkeys, farm animals, sport animals, pets, and other laboratory rodents and animals. Particularly preferred mammals are human, mice and rabbit. Preferred cells include stem cells of various cell types, such as, hematopoietic, muscle, epithelial, neural, liver, embryo and bone stem cells, particularly HSCs. Stem cells are capable of self-renewal divisions and give rise to differentiated progeny. They or their progeny contain the engrating potential for in vivo therapeutic application. Hematopoietic stem cells are pluripotent and may also be defined in vitro by the presence of CAFC activity. General reference is made to Potten C. S. ed., Stem Cells, Academic Press, 1997; Stem Cell Biology and Gene Therapy, eds. Quesenberry et al., John Wiley & Sons Inc., 1998; and Gage et al., Ann. Rev. Neurosci. 18:159–192, 1995.

Particularly preferred host cells include hematopoietic cells. These cells encompass hematopoietic stem cells, erythrocytes, neutrophils, monocytes, platelets, mast cells, eosinophils and basophils, B and T lymphocytes and NK cells as well as the respective lineage progenitor cells. T-cells are defined as a type of lymphocyte and are thought to develop from hematopoietic stem cells. There are many types of T-cells including thymocytes, helper T-cells, inducer T-cells, suppressor T cells, or any other subset of T-cells. As used herein the term progenitor or progenitor cell indicates a cell population which no longer is a stem cell but also which has not yet become a terminally differentiated cell. The term lymphoid, myeloid, or erythroid in conjunction with the term progenitor indicates the potential cell population into which the progenitor is capable of maturing. Human hematopoietic stem cells, T-cells and lymphoid, myeloid, or erythroid progenitor cells are especially preferred host cells.

Methods of obtaining hematopoietic cells and stem cells are well known in the art and not repeated herein in any detail. In general, methods of isolating stem cells and progenitor cells include isolation from other cells in hematopoietic tissue of the body and particularly bone marrow. Stem cells and progenitor cells from bone marrow constitute only a small percentage of the total number of hematopoietic cells. Stem cells appear to be in the range of about 0.01 to about 0.1% of the bone marrow cells. Bone marrow cells may be obtained from ilium, sternum, tibiae, femora spine and other bone cavities. Other non-limiting sources of hematopoietic stem cells include embryonic yolk sac, fetal liver fetal and adult spleen, blood including adult peripheral blood and umbilical cord blood (To et al., Blood 89:2233–2258 (1997)).

For the isolation of bone marrow an appropriate solution may be used to flush the bone, including but not limited to salt solution, supplemented with fetal calf serum or other naturally occurring factors in conjunction with an acceptable buffer at low concentration, generally about 5 to 25 mM. Buffers include but are not limited to HEPES, phosphate and lactate buffers. Bone marrow can also be aspirated from the bone in accordance with conventional techniques.

The manner in which hematopoietic cells may be separated from other cells is not critical to this invention. Various procedures may be employed and include physical separation, magnetic separation using antibody-coated magnetic beads, affinity chromatography, and cytotoxic agents joined to a monoclonal antibody or used in conjunction with a monoclonal antibody. Also included is the use of fluorescence activated cell sorters (FACS) wherein the cells can be separated on the basis of the level of staining of the particular antigens. These techniques are well known to those of ordinary skill in the art and are described in various references including U.S. Pat. Nos. 5,061,620; 5,409,8213; 5,677,136; and 5,750,397; and Yau et al., Exp. Hematol. 18:219–222 (1990).

The order of cell separation or selection is not critical to the invention, and specific cell types may be separated either prior to genetic modification or after genetic modification. Preferably cells are initially separated by a coarse separation followed by using positive and/or negative selection. In humans, the surface antigen expression profile of an enriched hematopoietic stem cell population may be identified by CD34$^+$Thy-1$^+$Lin$^-$. Other non-limiting enriched phenotypes may include: CD2$^-$, CD3$^-$, CD4$^-$, CD8$^-$, CD10$^-$, CD14$^-$, CD15$^-$, CD19$^-$, CD20$^-$, CD33$^-$, CD34$^-$, CD38$^{lo/-}$, CD45RA$^-$, $^{CD}$59$^{+/-}$, CD71$^-$, CDW109$^+$, glycophorin$^-$, AC133$^+$, HLA-DR$^{+/-}$, c-kit$^+$ and EM$^+$. Lin$^-$ refers to a cell population selected on the basis of lack of expression of at least one lineage specific marker, for example CD2, CD3, CD14, and CD56. The combination of expression markers used to isolate and define an enriched HSC population may vary depending on various factors and may vary as other expression markers become available.

Murine HSCs with similar properties to the human CD34$^+$ Thy-1$^+$Lin$^-$ may be identified by kit $^+$Thy-1.1$^{lo}$Lin$^{-/lo}$Sca-1$^+$ (KTLS). Other phenotypes are well known. When CD34 expression is combined with selection for Thy-1, a composition comprising approximately fewer than 5% lineage committed cells can be isolated (U.S. Pat. No. 5,061,620).

It has been shown CD34 is expressed on most immature T-cells also called thymocytes, and that these cells lack cell surface expression of CD1, CD2, CD3, CD4, and CD8 antigens. Also CD45RA is a useful T-cell marker. The most well-known T-cell marker is the T-cell antigen receptor (TCR). There are presently two defined types of TCRs, TCR-2 (consisting of α and β polypeptides) and TCR-1 (consisting of δ and γ polypeptides). B cells may be selected, for example, by expression of CD19 and CD20. Myeloid cells may be selected, for example, by expression of CD14, CD15, and CD16. NK cells may be selected based on expression of CD56 and CD16. Erythrocytes may be identified by expression of glycophorin A. Compositions enriched for progenitor cells capable of differentiation into myeloid cells, dendritic cells, or lymphoid cells also include the phenotypes CD45RA$^+$CD34$^+$Thy-1$^+$ and CD45RA$^+$CD10$^+$Lin$^-$CD34$^+$. One skilled in the art is aware of other useful markers for various cell types.

Once the host cells are harvested and optionally separated, the cells are cultured in a suitable medium comprising a combination of growth factors that are sufficient to maintain growth. The term culturing refers to the propagation of cells on or in media of various kinds. It is understood that the descendants of a cell grown in culture may not be completely identical (either morphologically, genetically or phenotypically) to the parent cell. Methods for culturing stem cells and hematopoietic cells are well known to those skilled in the art, and some of these methods are briefly mentioned herein. Any suitable culture container may be used, and these are readily available from commercial vendors. The seeding level is not critical, and it will depend on the type of cells used. In general, the seeding level will be at least 10 cells per ml, more usually at least about 100 cells per ml and generally not more than $10^6$ cells per ml.

Various culture media can be used and non-limiting examples include Iscove's modified Dulbecco's medium (IMDM), X-vivo 15 and RPMI-1640. These are commercially available from various vendors. The formulations may be supplemented with a variety of different nutrients, growth factors, such as cytokines and the like. In general, the term cytokine refers to any one of the numerous factors that exert a variety of effects on cells, such as inducing growth and proliferation. The cytokines may be human in origin or may be derived from other species when active on the cells of interest. Included within the scope of the definition are molecules having similar biological activity to wild type or purified cytokines, for example produced by recombinant means, and molecules which bind to a cytokine factor receptor and which elicit a similar cellular response as the native cytokine factor.

The medium can be serum free or supplemented with suitable amounts of serum such as fetal calf serum, autologous serum or plasma. If cells or cellular products are to be used in humans, the medium will preferably be serum free or supplemented with autologous serum or plasma. (Lansdorp et al., *J. Exp. Med.* 175:1501 (1992) and Petzer et al., PNAS 93:1470 (1996)).

Non-limiting examples of compounds which may be used to supplement the culture medium are thrombopoietin (TPO), Flt3 ligand (FL), c-kit ligand (KL, also known as stem cell factor (SCF) or Stl), Interleukin (IL) such as, IL-1, IL-2, IL-3, IL-6, (soluble IL-6 receptor), IL-11, and IL-12, granulocyte-colony stimulating factor (G-CSF), granulocyte macrophage-colony stimulating factor (GM-CSF), leukemia inhibitory factor (LIF), MIP-1α, and erythropoietin (EPO). These compounds may be used alone or in any combination, and preferred concentration ranges may be readily determined from the published art. When murine stem cells are cultured, a preferred non-limiting medium includes mIL-3, mIL-6 and mSCF.

One skilled in the art is aware of the concentration range of these compounds in cultures. While not meant to limit the invention a general preferred range of TPO is from about 0.1 ng/mL to about 500 µg/mL, more preferred is from about 1.0 ng/mL to about 1000 ng/mL even more preferred is from about 5.0 ng/mL to about 300 ng/mL. A preferred concentration range for each of FL and KL is from about 0.1 ng/mL to about 1000 ng/mL, more preferred is from about 1.0 ng/mL to about 500 ng/mL. IL-6 is a preferred factor to be included in the culture, and a preferred concentration range is from about 0.1 ng/mL to about 500 ng/mL and more preferred in from about 1.0 ng/mL to about 100 ng/mL. Hyper IL-6, a covalent complex of IL-6 and IL-6 receptor may also be used in the culture.

Other molecules can be added to the culture media, for instance, adhesion molecules, such as fibronectin or RetroNectin™ (commercially produced by Takara Shuzo Co., Otsu Shigi, Japan). The term fibronectin refers to a glycoprotein that is found throughout the body, and its concentration is particularly high in connective tissues where it forms a complex with collagen.

In a further aspect polypeptides of the invention may be produced by culturing the host cell comprising a polynucleotide of the invention under conditions suitable for the expression of the polypeptide and recovering said polypeptide from the host culture. Methods of obtaining polypeptides from host cells grown in culture are well known in the art.

In the present invention, the methods of genetic modification are intended to encompass any genetic modification method of exogenous or foreign gene transfer or nucleic acid transfer into mammalian cells (particularly human stem cell and hematopoietic cells). The term includes but is not limited to transduction (viral mediated transfer of host DNA from a host or donor to a recipient, either in vitro or in vivo), transfection (transformation of cells with isolated viral DNA genomes), liposome mediated transfer, electroporation, calcium phosphate transfection or coprecipitation and others. Methods of transduction include direct co-culture of cells with producer cells (Bregni et al., *Blood* 80:1418–1422 (1992)) or culturing with viral supernatant alone with or without appropriate growth factors and polycations (Xu et al., *Exp. Hemat.* 22:223–230 (1994)).

In a preferred embodiment the host cells are transduced with a retroviral vector as previously described. The host cell range that may be infected is determined by the viral envelope protein. The recombinant virus can be used to infect virtually any other cell type recognized by the env protein provided by the packaging cell, resulting in the integration of the viral genome in the transduced cell and the stable incorporation of the foreign gene product. In general, murine ecotropic env of MoMLV allows infection of rodents cells, whereas amphotropic env allows infection of rodent, avian and some primate cells including human cells. Amphotropic packaging of cell lines for use with MoMLV systems are known in the art and are commercially available. These include but are not limited to, PA12, PA317, ΨCRIP, and FLYA13. (See, Miller et al., *Mol. Cell Biol.* 5:431–437 (1985); Mill et al., *Mol. Cell Biol.* 6:2895–2902 (1986); and Danos et al., *Proc. Natl. Acad. Sci. USA* 85:6460–6464 (1988). Recently, the G-glycoprotein from vesicular stomatitis virus (VSV-G) has been substituted for the MoMLV env protein. (See Burns et al., *Proc. Natl. Acad. Sci. USA* 90:8033–8037 (1993); and WO92/14829). Xenotropic vector systems also exist which allow infection of human cells. The genetically modified cells obtained as described above may be used immediately, expanded or frozen at for example liquid nitrogen temperatures and stored for long periods of time, being thawed and capable of being used. The cells may be stored by methods well known in the art. Once the genetically modified cells are thawed they may be further expanded. Methods of expansion of HSCs by use of growth factors and/or stromal cells associated with stem cell proliferation and differentiation are well known to those skilled in the art (U.S. Pat. No. 5,744,361).

Methods of using the genetically modified cells include in vitro and in vivo applications. In one application, the invention further concerns, a method for increasing the effective dose of hematopoietic cells, particularly stem cells in a subject which includes obtaining a population of $CD34^+$ cells, including a subpopulation hematopoietic stem cells; introducing into the population of $CD34^+$ cells a polynucleotide sequence of the invention; obtaining a subpopulation of genetically modified stem cells which overexpress the polypeptide encoded by said polynucleotide; and administering said subpopulation of genetically modified cells to a mammalian subject wherein the effective dose of the hematopoietic stem cells is increased. Method of obtaining hematopoietic cells has previously been disclosed. The HSC may be selected using various known and previously mentioned techniques either prior to or after genetic modification. As an example the hematopoietic cells may be isolated based on phenotype expression as disclosed hereinabove. In a preferred embodiment the polynucleotide is introduced on a vector. While any method of genetic modification may be used to introduce a polynucleotide of the invention into the host cells, transduction is the preferred method of genetic modification.

An "effective amount or dose" is an amount sufficient to effect beneficial or desired results. An effective amount may be administrated in one or more administrations. Determination of an effective amount is within the capability of those skilled in the art. Particularly preferred subjects of the invention in general include living mammals such as human, mice and rabbit, most preferred are humans. The administration of a genetically modified cell comprising a polynucleotide sequence of the invention may be by conventional means, for example, injection, oral administration, inhalation and others. Appropriate carries and diluents may be included in the administration of the modified cells. Samples including the modified cells and progeny thereof may be taken and tested to determine transduction efficiency. The population of CD34$^+$ cells may be cultured either prior to or after genetic modification of the host cells.

As used herein the term "overexpression" refers to expression of a polypeptide of the invention brought about by genetic modification of a host cell with a nucleic acid sequence encoding the polypeptide. Particularly preferred are polynucleotides that encode SCM 3, SCM 26, SCM 113 and functionally equivalent polypeptides having 85% identity thereto. Overexpression may take place in cells normally lacking expression of polypeptides functionally equivalent or identical to the SCM proteins claimed herein or overexpression may take place in cells with endogenous expression of polypeptides functionally equivalent or identical to the SCM protein claimed herein. While overexpression may take place in any cell type particularly preferred host cells include hematopoietic cells, particularly HSCs and T-cells. For example, a HSC may have an endogenous level of expression of functionally equivalent or identical polypeptide to a SCM protein, but the host cell would not be genetically modified to include a nucleic acid sequence of the invention encoding a SCM polypeptide and capable of expression thereof.

As used herein a "wild type" cell is a cell type of the host cell but not genetically modified to include a polynucleotide sequence encoding a SCM polypeptide of the invention and would not result in overexpression. The overexpression of SCM proteins can be measured by various methods well known in the art. A preferred method includes the measurement of a marker gene particularly EGFP by FACS.

The method may also provide the introduction of a second polynucleotide sequence encoding a therapeutic gene, an antisense gene or a ribozyme into the population of CD34$^+$ cells as described herein above. In another application the invention concerns a method of increasing the effective dose of gene modified cells. Host cells and particularly hematopoietic stem cells overexpressing the polynucleotides of the invention are useful therapeutically. Differentiation of the cells is blocked resulting in expansion of non-differentiated stem cells. Expansion of non-differentiated stem cells gives an increase in stem cell dose either ex vivo or in vivo, thereby potentially allowing more rapid engraftment. This may result in increased representation of genetically modified cells in a subject.

The genetically modified host cells are maintained for a period of time sufficient for overexpression of SCM proteins. A suitable time period will depend inter alia upon cell type used and is readily determined by one skilled in the art. In general, genetically modified cells of the invention may overexpress SCM proteins for the lifetime of the host cell. Preferably, for hematopoietic cells the time period will be in the range of 1 to 45 days, more preferably in the range of 1 to 30 days, even more preferably in the range of 1 to 20 days, still more preferably in the range of 1 to 10 days, and most preferably in the range of 1 to 5 days.

A further application of the invention concerns a method of blocking the differentiation of mammalian hematopoietic stem cells including introducing a polynucleotide sequence of the invention into CD34$^+$ cells; genetically modifying a population of the CD34$^+$ cells; allowing expression of the polynucleotide sequence in the cells; and blocking differentiation of said genetically modified cells. Preferably the polynucleotide will encode SCM 3, SCM 26, SCM 113 or functionally equivalent polypeptides thereto.

As discussed above stem cells are pluripotent and capable of self-renewal. Differentiation is defined as the restriction of the potential of a cell to self renew with a change in the functional capacity of the cell. The term "blocking" differentiation is used broadly in the context of this invention and includes not only the prevention of differentiation but also means the altering of differentiation. Differentiation may be determined by methods well known in the art and these include analysis for surface markers associated with cells of a defined differentiated state. While not meant to limit the invention, generally differentiation will be slowed to about at least 10%, preferably to about 15%, more preferably to about 20%, and most preferably to about 30% or greater fewer cells expressing a specific differentiation marker. Such markers include, for example, CD4, CD8, CD13, CD14, CD19, CD36, CD40, CD41 and CD94. In a preferred embodiment, differentiation will be slowed to about at least greater than 15% and preferably greater than 20%, fewer cells expressing the marker CD14.

The method of blocking the differentiation of mammalian hematopoietic stem cells may also include isolating hematopoietic cells, particularly CD34$^+$ cells from a source of such cells and introducing a polynucleotide of the invention into the cells whereby the cells are genetically modified. Additionally it is preferred that the polynucleotide be introduced on a vector, preferably a retroviral vector wherein the host cells are genetically modified by transduced. However it is emphasized that may different vector systems as discussed above may be used in the method. Once the cells are genetically modified they are cultured in the presence of at least one cytokine in an amount sufficient to support growth of the modified cells and the modified cells are selected wherein the encoded polypeptide is overexpressed and differentiation is blocked.

Figure 3A:
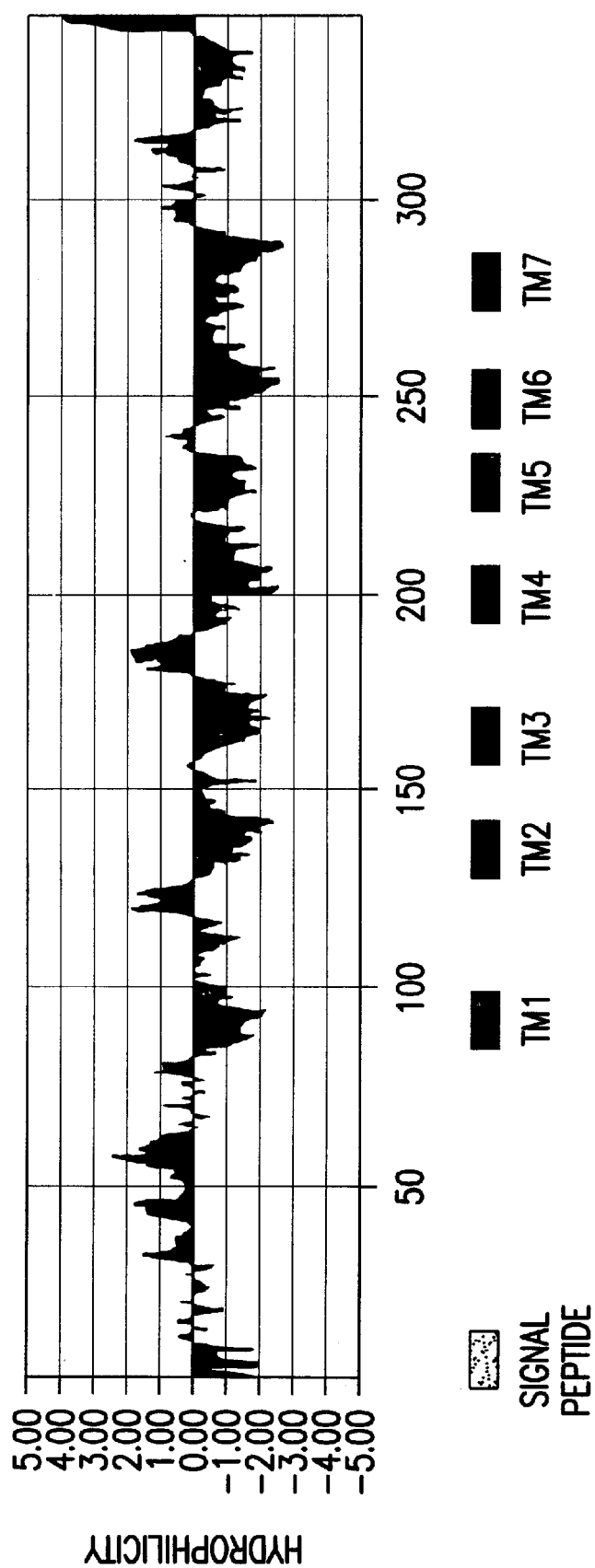
FIGS. 3A–C.
Figure 3B:
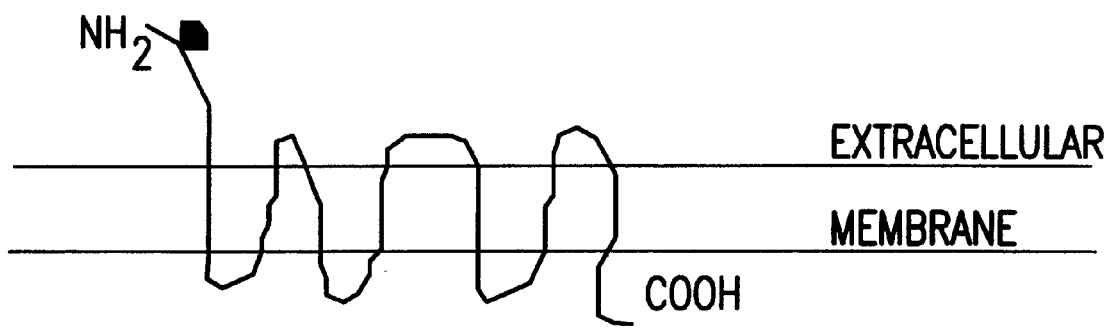
Figure 3C:
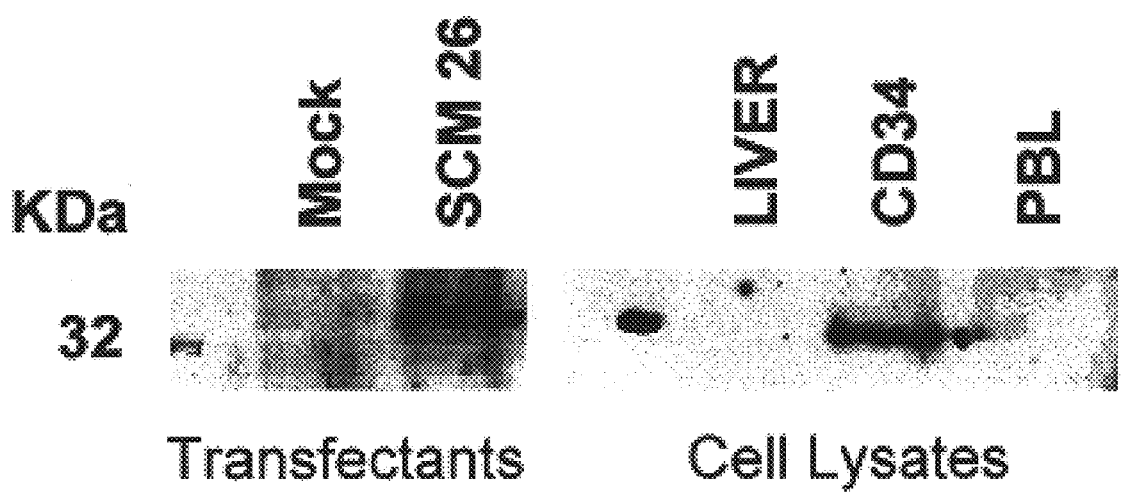

The invention still further includes an antibody which binds to the polypeptides of the invention. As used herein the term SCM antibody encompasses any antibody or fragment thereof either native or recombinant, synthetic or naturally derived, which retains sufficient specificity to bind specifically to the SCM protein. The SCM antibody may be monoclonal or polyclonal that binds to SCM protein. In this regard the antibody recognizes, preferentially hematopoietic cells, particularly stem cells. For the production of antibodies, various host subjects, may be immunized by injection with SCM 3, 26 or 113 protein, or a fragment or variant thereof. General techniques for the production of antibodies are known and various protocols for measuring protein are also known including enzyme linked immunosorbant assay and fluorescent activated cell sorting. While the protein as illustrated in FIG. 2, 4 or 6 may be used to raise antibodies. The protein sequence of SCM 26 is most preferred. In the present invention, a polyclonal antiserum against SCM 26 amino acid residues 26–40 was raised in rabbits using well known techniques. Peptide specific antibodies were purified by affinity chromatography and used for immunoblots or wildtype fibroblast or fibroblasts transfected with a retroviral vector expressing SCM 26, FIG. 3. The same antibody was used to probe lysates of Liver, CD34$^+$ cells or peripheral blood leukocytes (FIG. 3). Additionally extracellular regions of SCM26 may be used to generate antibodies that might be useful to detect cell surface SCM26 proteins; such fragments include amino acid sequences 25 through 82; 147 through 157 and 266 through 275 of the amino acid sequence illustrated in FIG. 2.

Selecting antibodies particularly monoclonal antibodies are particularly useful for identifying markers associated with particular cell lineages and/or stages of differentiation. The antibodies may attach to a solid support to allow crude separation. The separation techniques employed should maximize the retention of viability of a fraction to be collected Therefore, the invention encompasses not only antibodies which bind to a polypeptide of the invention but also a method of identifying stem cells, particularly hematopoietic stem cells or the progeny thereof. This includes preparing an antibody to a polypeptide of the invention, purifying the antibody, exposing a population of hematopoietic cells to the antibody allowing the exposed cells to bind with the antibody and then selecting bound cells. Techniques including antibody preparation and purification are well known in the art and these techniques are preformed on a routine basis. Reference is made to Antibodies: A Laboratory Manual, Harlow et al., eds. (1987).

The genetically modified cells obtained by the methods herein described may be further used in an autologous or allogenic setting wherein the optionally expanded, modified cells are then used for example in bone marrow transplantation, graft facilitation, or immune reconstitution.

Furthermore various in vitro and in vivo assays are well known in the art for the measurement of the functional compositions of hematopoietic cell populations. (Reference is made to Quesenberry et al. eds., Stem Cell Biology and Gene Therapy, Wiley-Liss Inc. 1998—Chapter 5, Hematopoietic Stem cells: Proliferation, Purification and Clinical Applications, pgs 133–160) Non-limiting examples of these assays are briefly described herein below. The long term culture-initiating cell (LTCIC) assay involves culturing a cell population on stromal cell monolayers for approximately 5 weeks and then testing in a 2 week semisolid media culture for the frequency of clonogenic cells retained (Sutherland et al., Blood 74:1563 (1989)). The Colony-Forming Unit Culture (CFU-C) assay involves use of cell count as the number of colony-forming units per unit volume or area of a sample The assay is used to measure clonal growth of quickly maturing progenitors in semi-solid media supplemented with serum and growth factors. Depending on the growth factors used to stimulate growth mature and/or primitive progenitors may be determined. Cobblestone area forming colony (CAFC) assays measure clonal proliferation of long-lived progenitors supported by stromal cell monolayers and growth factor/serum supplemented media. On the appropriate stromal monolayers, cells pluripotent for myeloid and lymphoid lineages may be determined. (Young et al., Blood 88:1619, (1996)). SCID-hu bone assays measure the proliferation and multilineage differentiation of cells with bone marrow repopulating activity. These cells are likely to contribute to durable engraftment in clinical transplantation. SCID-hu thymus assays measure the proliferation and differentiation in thymocytes. Both bone marrow repopulating and more mature T-lineage progenitors may be measured.

The practice of the present invention will employ, unless otherwise indicated conventional techniques of cell biology, molecular biology, cell culture, immunology and the like which are in the skill of one in the art. These techniques are fully disclosed in the current literature and reference is made specifically to Sambrook, Fritsch and Maniatis eds., "Molecular Cloning A Laboratory Manual, 2nd Ed., Cold Springs Harbor Laboratory Press, 1989); the series Methods of Enzymology (Academic Press, Inc.); and Antibodies: A Laboratory Manual, Harlow et al., eds., (1987).

All publications and patent applications mentioned in this specification are indicative of the level of skill of those skilled in the art to which this invention pertains. All publications and patent applications cited herein are hereby incorporated by reference in their entirety in order to more fully describe the state of the art to which this invention pertains.

The invention generally described above will be more readily understood by reference to the following examples, which are hereby included merely for the purpose of illustration of certain embodiments of the present invention and are not intended to limit the invention in any way

EXPERIMENTAL

Example 1: cDNA Library Construction

Following informed consent, human donors were treated with cyclophosphamide plus granulocyte-macrophage colony stimulating factor (GM-CSF) to mobilize CD34$^+$ Thy-1$^+$ hematopoietic stem cells (HSCs) to the peripheral blood. HSCs from multiple donors were combined. After apheresis, CD34$^+$Thy-1$^+$HSC stem cells were purified by flow sorting as described by Gazitt et al., Blood, 86:381–389 (1995). Total RNA was purified from >10$^7$ HSC using RNA-Stat (Tel-Test B inc, Friendswood, Tex.). PolyA$^+$ RNA was purified from total RNA on oligo dT (Pharmacia Biotech) and used to synthesize cDNA (Stratagene unidirectional cDNA synthesis kit). Each cDNA molecule generated using this kit has an EcoR1 sticky end at the 5' end and a Xho1 sticky end at the 3' end. The cDNA was directionally cloned into lambda ZAP express that had been digested with EcoR1 and Xho1 restriction enzymes (Stratagene). The ligated cDNA/lambda ZAP was packaged using Gigapack III gold (Stratagene) and transfected into XL1-Blue MRF's cells (Stratagene). A total of 0.5×10$^6$ independent clones were produced. The lambda phage were harvested and in vivo excised to pBlueScript (pBS) using ExAssist helper phage and SOLR strain E. coli according to recommended Stratagene protocol.

Random clones were mini prepped by Qiagen 96 well system, restriction digestion with EcoR1 plus XhoI and electrophoresed to show inserts in the size range 0.5–5.0 Kb with an average size of 2.3 Kb. 10,000 mini prep clones were sequenced using T3 primed (i.e. 5' end) dye terminator sequencing reactions and processed on an ABI377 automated sequencer (PE Applied Biosystems). Sequence data was analyzed by BLASTX and BLASTN (Basic Local Alignment Search Tool) searches against GenBank. A number of clones were identified as being either completely novel or having homology only with ESTs.

Expression profiling was used to identify cDNA sequences which are preferentially expressed in HSCs. The cDNA inserts of clones identified as being either completely novel or having homology only with expressed sequence tags (ESTs) were amplified by PCR using T3 and T7 primers and then sent to Synteni were the microdot arrays were generated. Microdot array probes were synthesized from RNA purified from mobilized peripheral blood CD34+ cells and labeled with Cy3 and from either peripheral blood cells (PBL) RNA or CD11b RNA or CD4 RNA or CD19 RNA and labeled with Cy5 using standard protocols as recommended by Synteni. The CD34 probe and the PBL probe were mixed and allowed to hybridize to a microdot array. After hybridization and washing, the microarray was scanned to determine the intensity of probe binding to each cDNA. Hybridizations, washing and scanning were performed by Synteni. Probe binding is proportional to gene expression level. The raw binding data was balanced by monitoring probe binding to Synteni control elements on the microarray; this accounts for differences in the fluorescent labeling of the two probes. The ratio of the two binding intensities, the balanced differential expression (BDE) gives a quantitative measurement of relative gene expression level. Table 1 shows the differential expression of SCM3 in 3 independent experiments. Similar results were observed for SCM26 and SCM113 (data not shown).

TABLE 1

Expression profiling of SCM3 in three independent experiments.

| Experiment | CD34 Probe Value | PBL probe value (Balanced value) | Balanced differential expression (BDE) |
| --- | --- | --- | --- |
| 1 | 10669 | 1944 | 5.5 |
| 2 | 21687 | 9271 | 2.3 |
| 3 | 10849 | 4681 | 2.3 |

Analysis allowed the identification of 101 new cDNAs that were expressed more in stem cells than in peripheral blood cells (PBL), these cDNAs were designated selected cDNAs. The selected cDNAs are defined as being expressed at least two fold higher in stem cells (BDE>2.0) and have a low expression in PBL cells. The control cDNAs, CD34, flk2 (fetal liver kinase) and KIT (stem cell factor or alternatively steel factor, or c-Kit ligand) are known to be preferentially expressed in HSC and this is confirmed using transcript imaging.

Two approaches were taken to prioritize the 101 selected cDNAs: sequence analysis was used to confirm their new classification and further transcript imaging experiments were performed to investigate levels of expression in subsets of peripheral blood cells. Microdot arrays were analyzed with probes specific for CD34+ cells compared with either T cells (CD3+), B cells (CD19+) or myeloid cells (CD11b+). High priority cDNAs were confirmed to be novel and had HSC-restricted expression (i.e. relatively low expression in PBL, B, T and myeloid cells). Three clones are herein identified as SCM 26, SCM 3, and SCM 113. The cDNA insert in each clone is illustrated in FIGS. 2, 4, and 6 and correspond to SEQ ID Nos. 1, 3 and 5.

Example 2: Vector Construction cDNA inserts were subcloned from pBS and into an MSCV based retroviral vector (Hawley et al., *Gene Therapy,* 1:136–138 (1994). The cDNA inserts were subcloned into vector MIE. (See FIG. 1). MIE was constructed from MINGFR (Cheng et al., *Blood* 92:83–92 (1998) by removing the nerve growth factor receptor (NGFR) gene and replacing it with enhanced green fluorescent protein (EGFP) gene on a 707bp Nco1-blunted Bsp1 fragment. The NGFR gene was replaced by restriction digestion with ClaI, filling in the sticky end and then digestion with Nco1. The EGFP was isolated from pEGFP-1 (Clontech) and has GenBank Accession No. U55761. MIE vector has the essential components LTR-IRES-EGFP. The cDNA inserts are cloned into MIE at the EcoR1 site by PCR of the coding region of either SCM3, SCM26 and SCM113 and cloning to PCR2, removal from PCR2 by EcoR1 digestion and ligation into MIE. This gives gene expression mediated by the LTR and the ribosome entry site (IRES) allows for simultaneous translation of both the gene of interest and EGFP proteins from one primary transcript. Expression of EGFP allowed selection of transduced cells by FACS.

The SCM3 cDNA fragment containing the entire coding region of SEQ ID NO. 3 was amplified by PCR and the 3' primer included an in fame hemaglutining (HA) tag (5' TAC CCC TAC GAC GTG CCC GAC TAC GCC—SEQ ID NO. 7) followed by a stop codon, was subcloned into the MIE vector at the EcoR1 site. Additionally 3' and 5' truncations of the SCM 3 gene have been made. The 5' fragment lacks the DNA binding region. The fragment is illustrated in FIG. 2 from nucleotide residue 81 to nucleotide residue 783. The 3' fragment is the zinc finger domain from nucleotide residue 784 to nucleotide residue 1710. Vectors including the 5' and 3' fragments were constructed as described above for the full length SCM 3 except that for the 3' fragment the 5' PCR primer included an in frame ATG start codon. The HA tag and anti-HA antibodies were used to follow protein expression by western blots. The SCM 26 cDNA fragment containing the entire coding region of SEQ ID NO.1 was cloned out of pBS by digestion with Smal and Xho1. MIE was digested with EcoR1, the sticky ends filled in, and then digested with Xho1. The SCM26 fragment was ligated into the blunt/Xho1 cut MIE. The SCM 113 cDNA fragment containing the entire coding region of SEQ ID NO. 5. was cloned into MIE as described above for SCM3.

Example 3: Retroviral Infection

The retrovirus was produced by transfecting retroviral vector into the RV packaging cell line phoenix (Kinsella et al., *Human Gene Therapy,* 7(12):1405–1413, 1996) obtained from Nolan Laboratories using standard transfection protocols (Promega). Viral supernatant was collected after 48 hours.

Following informed consent, leukaphersis samples were obtained from normal adult donors mobilized with 7.5 or 10.0 μg/kg/day of granulocyte-colony stimulating factor (G-CSF) for 5–6 days. CD34+ cells were enriched from leukaphersis samples at SyStemix (Palo Alto, Calif.) using Isolex 300SA or 300I (Baxter Healthcare Corp., Deerfield Ill.) as described in Young et al., *Blood,* 88:1619–1631, (1996), and by methods well-known in the art.

The CD34+ cells were cultured at $2 \times 10^6$ cells per ml in 10 mL cultures in serum free ex-vivo 15 medium (BioWhittaker, Walkerville, Md.) for 48 hours at 37° C. and 5% $CO_2$. The cultures were supplemented with TPO, 100 ng/mL (R & D Systems, Minneapolis, Minn.); SCF, 100 ng/mL (SyStemix, Palo Alto Calif.); Flt3-L, 100 ng/mL (SyStemix, Palo Alto Calif.); and IL-6, 20 ng/mL as described in Luens et al., *Blood,* 91(4):1206–1215 (1998).

After the 48 hours, the cells were centrifuged for 5 minutes at 4000 rpm at 37° C. and resuspended in the same medium described directly above. The cells were added to fibronectin fragment CH-296 (FN) (BioWhittaker, Walkerville, Md.) coated plates (10 μg/mL) containing an equal volume of retroviral supernatant for 20 hour culture at 37° C. in 5% $CO_2$ without polybrene or protamine sulphate. (Hanenburg et al., *Human Gene Therapy*, 8:2193–2206, 1997). Cells were washed and incubated for an additional 72 hours with serum free ex-vivo 15 medium (BioWhittaker, Walkerville, Md.) supplemented with TPO, 100 ng/mL; SCF, 100 ng/mL; Flt3-L, 100 ng/mL; and IL-6, 20 ng/mL. After incubation the $CD34^+$ cells or in some cases the $Thy-1^+$ cells expressing EGFP were purified by flow cytometry and placed into different functional assays as described below. Controls included cells transduced in parallel cultures with MIE vector containing only the EGFP.

Retroviral transduction resulted in constitutive stable expression of EGFP (at least for 6 weeks) with almost no decay. This was confirmed by fluorescence activated sorting (FACS) of cells following extended cultures. Expression of SCM 3 and 26 was confirmed by western blotting.

Example 4: Cell sorting

Cells were stained with anti-CD34-APC MoAb or isotype control. (Becton Dickinson). The staining buffer was HBSS/2% fetal calf serum (FCS) and 10 mmol/L HEPES for 20 minutes on ice together with anti-Thy-1 (GM201) PE-conjugated MoAb at 5 μg/mL. Cells were washed twice in SB and then resuspended in SB with propidium iodide (10 μg/mL. Cells were sorted on the FACSTAR Plus cell sorter (Becton Dickinson, San Jose, Calif.). EGFP fluorescence was detected in the FITC channel. $CD34^+$ and $CD34^-$ regions as well as $Thy-1^+$ and $Thy-1^-$ were set using the isotype controls. Cell populations from the $EGFP^+$ region were selected after removal of cells of high propidium iodide uptake and electronically gating on $CD34^+$ cells (or $Thy-1^+$ subset of $CD34^+$ cells). Reanalysis of the sorted cells indicated a purity greater than 90% for EGFP $CD34^+$, and ranging from 60% to 95% for $Thy-1^+$ after sorting for $EGFP^+Thy-1^+$ cells.

Example 5: Liquid Culture Assays

After sorting, cells were counted using a hemocytometer and 40,000 or 60,000 cells were incubated in ex-vivo media with TPO (100 ng/mL), SCF (100 ng/mL), FL (100 ng/mL), IL-6 (20 ng/mL) at a cell concentration of $0.2 \times 10^6$/mL. At days 3, 6, 10, 14, and 21 the number of alive and dead cells were counted by trypan blue exclusion. These methods are well known in the art. Cells were then plated at $0.2 \times 10^6$/mL.

Figure 7:
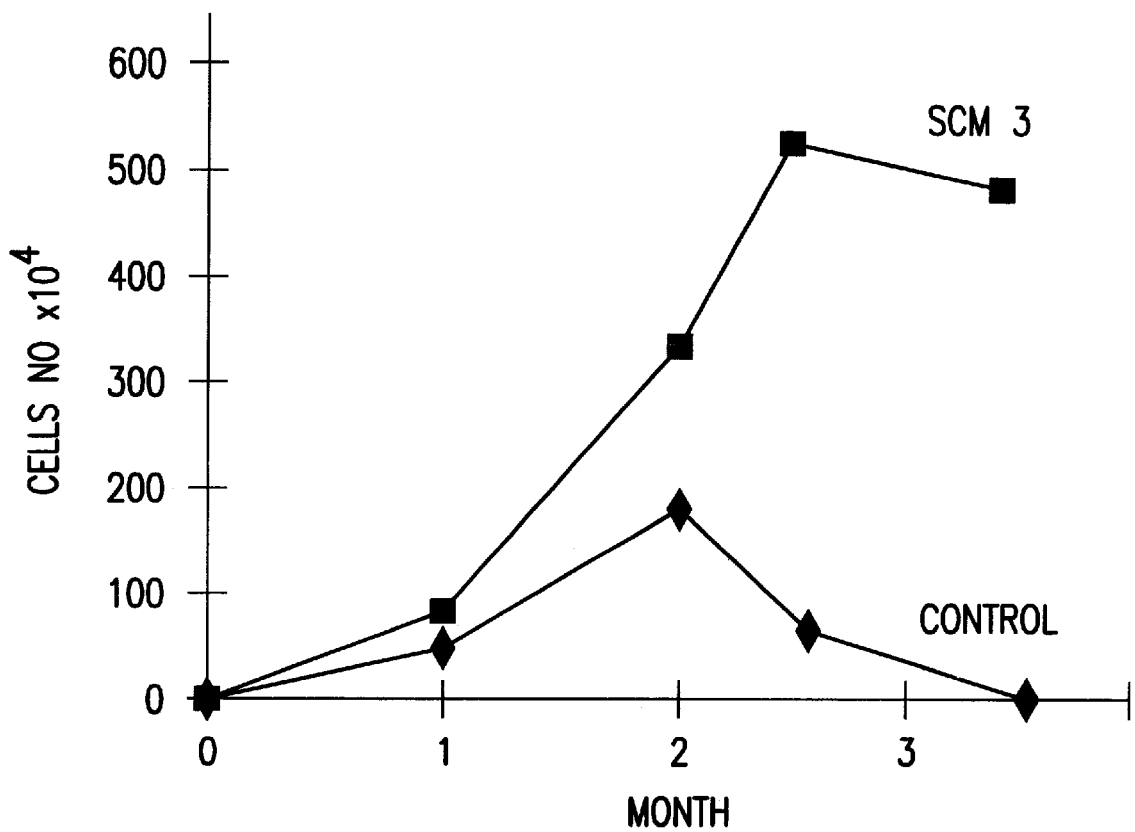
FIG. 7 illustrates sustained proliferation of genetically modified cells grown in liquid culture and incorporating a polynucleotide sequence encoding SCM 3.

The expression of SCM 3 had a positive effect on cell expansion after 2 weeks of culture. While overexpression of SCM 3 had little effect during the first 7 days of culture, by 14 days, cultures of SCM 3 expressing cells showed enhanced viability and proliferation. This effect continued for 2 months. SCM 3 expressing cells continued to grow while control cells stopped proliferation (FIG. 7). After 6 weeks of liquid culture, the number of clonogenic cells (CFU-C) was determined (See Example 6). Cells overexpressing SCM3 were 20 fold enriched in CFU-C frequency in comparison with control cells.

Example 6: CFU-c Assays

To determine the effect of SCM 3, SCM 113 or SCM 26 overexpression on expansion of progenitor cells, EGFP expressing cells or control cells were sorted and placed into CFU-C assays. This assay enumerates the colonies (clonogenic cells) that grow in the presence of hematopoietic growth factors (colony stimulating factors and interleukins) from cells suspended in a semi-solid medium (methylcellulose). Enumeration of clonogenic cells (CFU-C) is a widely practiced assay for progenitor content.

CFU-C assays used MethoCult H4230 methylcellulose (Stem Cell Technologoies Inc., Vancouver, Canada V5Z4J7) supplemented with IL-3 (10 ng/mL); IL-6 (10 ng/mL); SCF (100 ng/mL); and EPO (2 U/mL). Sorted cells were plated in 35 mm dishes, in triplicate at 500 cells/dish. Colonies (>50 cells) were counted 14 days after plating and an average from 3 dishes were taken for each experimental condition. The colonies were classified as CFU-M (myeloid like), CFU-E (erythoid like), or CFU-Mix (mixed).

Overexpression of SCM 3 resulted in slightly reduced CFU-C frequency. Consistently observed in seven different experiments, was a 30% decrease in the number of CPU-M (difference significant), CFU-E (difference is not significant) and no decrease in number of more primitive CFU-MIX.

Overexpression of SCM 113 resulted in 40% decrease in the total CFU-C, significantly for both erythroid and myeloid lineages. Overexpression of SCM 26 resulted in a 25% decrease in the total number of CFU-C. Overexpression of SCM 26 also resulted in a decrease in number of single lineage colonies: 30% decrease in erythroid colonies, 2-fold decrease in myeloid colonies. In contrast SCM 26 overexpression gave 2-fold increase in the number of mixed type colonies in CFU-C assays (difference significant). Data not shown.

Example 7: Replating of CFUC to Secondary Colonies

To further assess biological potential, cells from methylcellulose were harvested and plated into secondary cultures with IL-3 (10 ng/mL); IL-6 (10 ng/mL); SCF (100 ng/mL); and EPO (2 U/mL). After 14 days in culture, cells were harvested from methylcellulose by washing dishes 2× with Phosphate Buffered Saline (Dubecco), and replated at 10 000 cells/dish into methylcellulose culture, as described above. Overexpression of SCM3 increased the number of secondary colonieg 4.7 fold compared to control cells. Similar results were seen with SCM 26 and SCM 113. Expression of SCM 113 increased the number of secondary colonies after replating 4.6 fold. Overexpression of SCM 26 increased replating efficiency, on average by 4.5 fold.

Example 8: Phenotypic Analysis of Cells After Methylcellulose or Liquid Culture

After CFU-C assay and following 14 days of liquid culture, the impact of SCM 3 overexpression on myeloid differentiation was assessed using FACS analysis. Cells were harvested and stained for expression of differentiation markers (Cell surface markers, CD14, CD13 and CD33 as described in Barclay et al., *The Leucoycte Antigen Facts Book*, Academic Press, pp 132, 130,174 (1993)). Reference is also made to Becton Dickinson. Monoclonal Antibody Source Book—published by Becton Dickinson Immunocytometry Systems—San Jose, Calif. 95131-1807).

Expression of SCM 3 gene resulted in inhibition of myeloid differentiation of hematopoietic progenitor cells (Table 2). On average, overexpression of SCM 3 resulted in a 2-fold decrease in percentage and absolute number of cells expressing myeloid markers (CD14, Table 2 and CD13, data not shown). This was observed after 2 or 3 weeks culturing in methylcellulose in the presence of GM-CSF, IL-6, IL-3, SCF, EPO or in liquid culture in the presence of TPO, Flt3, CSF, IL-6 (difference significant). The absolute level of expression (mean of fluorescence) was also decreased (data not shown). Similar results were seen for SCM26 and SCM113.

TABLE 2

CD14 expression following culture.
Fold Reduction in CD14 expression after culture relative to control cells.

|  | MIE Control | SCM3 | SCM113 | SCM26 | SCM 3 (AA 240–543) |
|---|---|---|---|---|---|
| Liquid culture | 1 | 1.85 | 7.06 | 2.0 | ND |
| Methyl cellulose | 1 | 2.28 | 4.85 | 5.08 | 3.7 |

Table 2 shows data on CD14+ expression on cells with overexpression of SCM3, SCM113, SCM26 and amino acid residues 240–543 of SCM3. The fold reduction in CD14 expression level is shown relative to cells transduced with control MIE vector alone.

Example 9: SCID-bono Assays

Transduced cells as described above were injected into irradiated SCID-hu mice. The SCID bone assay was preformed as described by Murray et al., *Blood,* 85:368, 1995. C.B.-17 scid/scid mice were used as recipients of human fetal bone grafts. Limiting dilution analysis was preformed to determine the dose SCM3, SCM26 or SCM113 expressing cells or control cells that will give donor reconstitution in the SCID-hu bone model. Fetal bone grafts are injected with cell doses of 5,000, 10,000, and 30,000 cells per graft into mice that receive whole body irradiation (350 rads) shortly before cell injection. Cells were not sorted for EGFP expression. At six weeks after injection the bone grafts are recovered, and the bone marrow cells are harvested and analyzed for donor cell engraftment using EGFP fluorescence and by methods well known in the art.

Example 10: Production of SCM Antibodies

A polyclonal antibody to a SCM 26 fragment corresponding to amino acid residues 25–82 of SEQ ID No. 2. was generated and used to immunize rabbits by methods well known in the art. (Antibodies: A Laboratory Manual, Harlow et al. eds., (1987).

What is claimed is:

1. An isolated polynucleotide sequence encoding a polypeptide comprising a sequence selected from the group consisting of
   a) the amino acid sequence of SEQ ID NO: 4;
   b) the amino acid sequence of residues 240–543 of SEQ ID NO: 4; and
   c) the amino acid sequence of SEQ ID NO: 6.

2. An isolated DNA sequence comprising a nucleotide sequence selected from the group consisting of
   a) the polynucleotide sequence of SEQ ID NO: 1;
   b) the polynucleotide sequence of SEQ ID NO: 3; and
   c) the polynucleotide sequence of SEQ ID NO: 5.

3. A host cell comprising the polynucleotide of claim 1 or the isolated DNA sequence of claim 2.

4. An isolated polynucleotide sequence consisting of the complement of the DNA sequence of claim 2.

5. A vector comprising the polynucleotide sequence of claim 1 or the isolated DNA sequence of claim 2.

6. The vector according to claim 5 wherein the vector is a retroviral vector.

7. A host cell comprising the vector of claim 5.

8. A method of producing the polypeptide encoded by the DNA sequence of claim 2, comprising the steps of:
   a) culturing a host cell comprising the DNA sequence of claim 2 under conditions suitable for the expression of the polypeptide, and
   b) recovering said polypeptide from the host culture.

9. An isolated DNA sequence which encodes an isolated polypeptide comprising a member selected from the group consisting of
   a) the amino acid sequence of SEQ ID NO: 4;
   b) the amino acid sequence of residues 240–543 of SEQ ID NO: 4; and
   c) the amino acid sequence of SEQ ID NO: 6.

10. A method of producing the polypeptide encoded by the isolated DNA sequence of claim 9, comprising the steps of:
   a) culturing a host cell comprising the DNA sequence of claim 9 under conditions suitable for the expression of the polypeptide, and
   b) recovering said polypeptide from the host culture.

11. An isolated polynucleotide sequence encoding the amino acid sequence of SEQ ID NO: 6.

12. An isolated DNA sequence comprising the polynucleotide sequence of SEQ ID NO: 5.

13. A vector comprising a polynucleotide sequence encoding the amino acid sequence of SEQ ID NO: 6.

14. A host cell comprising a polynucleotide sequence encoding the amino acid sequence of SEQ ID NO: 6.

15. A method of producing the polypeptide of SEQ ID NO: 6, comprising the steps of:
   a) culturing a host cell comprising a polynucleotide seqence encoding the polypeptide of SEQ ID NO: 6 under conditions suitable for the expression of the polypeptide; and
   b) recovering said polypeptide from the host culture.

* * * * *

SEQUENCE LISTING

<160> NUMBER OF SEQ ID NOS: 7

<210> SEQ ID NO 1
<211> LENGTH: 1316
<212> TYPE: DNA
<213> ORGANISM: Homo sapiens

<400> SEQUENCE: 1

```
cggggaccga gcatttcaga tctgctcggt agacctggtg caccaccacc atgttggctg      60
caaggctggt gtgtctccgg acactacctt ctagggtttt ccacccagct ttcaccaagg     120
cctcccctgt tgtgaagaat tccatcacga agaatcaatg gctgttaaca cctagcaggg     180
aatatgccac caaaacaaga attgggatcc ggcgtgggag aactggccaa gaactcaaag     240
aggcagcatt ggaaccatcg atggaaaaaa tatttaaaat tgatcagatg ggaagatggt     300
ttgttgctgg aggggctgct gttggtcttg gagcattgtg ctactatggc ttgggactgt     360
ctaatgagat tggagctatt gaaaaggctg taatttggcc tcagtatgtc aaggatagaa     420
ttcattccac ctatatgtac ttagcaggga gtattggttt aacagctttg tctgccatag     480
caatcagcag aacgcctgtt ctcatgaact tcatgatgag aggctcttgg gtgacaattg     540
gtgtgacctt tgcagccatg gttggagctg gaatgctggt acgatcaata ccatatgacc     600
agagcccagg cccaaagcat cttgcttggt tgctacattc tggtgtgatg ggtgcagtgg     660
tggctcctct gacaatatta gggggtcctc ttctcatcag agctgcatgg tacacagctg     720
gcattgtggg aggcctctcc actgtggcca tgtgtgcgcc cagtgaaaag tttctgaaca     780
tgggtgcacc cctgggagtg ggcctgggtc tcgtctttgt gtcctcattg ggatctatgt     840
ttcttccacc taccaccgtg gctggtgcca ctcttactc agtggcaatg tacggtggat     900
tagttctttt cagcatgttc cttctgtatg atacccagaa agtaatcaag cgtgcagaag     960
tatcaccaat gtatggagtt caaaaatatg atcccattaa ctcgatgctg agtatctaca    1020
tggatacatt aaatatattt atgcgagttg caactatgct ggcaactgga ggcaacagaa    1080
agaaatgaag tgactcagct tctggcttct ctgctacatc aaatatcttg tttaatgggg    1140
```

```
cagatatgca ttaaatagtt tgtacaagca gctttcgttg aagtttagaa gataagaaac    1200
atgtcatcat atttaaatgt tccggtaatg tgatgcctca ggtctgcctt tttttctgga    1260
gaataaatgc agtaatcctc tcccaaataa gcacacacaa aaaaaaaaaa aaaaaa        1316
```

<210> SEQ ID NO 2
<211> LENGTH: 345
<212> TYPE: PRT
<213> ORGANISM: Homo sapiens

<400> SEQUENCE: 2

```
Met Leu Ala Ala Arg Leu Val Cys Leu Arg Thr Leu Pro Ser Arg Val
 1               5                   10                  15

Phe His Pro Ala Phe Thr Lys Ala Ser Pro Val Val Lys Asn Ser Ile
                20                  25                  30

Thr Lys Asn Gln Trp Leu Leu Thr Pro Ser Arg Glu Tyr Ala Thr Lys
        35                  40                  45

Thr Arg Ile Gly Ile Arg Arg Gly Arg Thr Gly Gln Glu Leu Lys Glu
    50                  55                  60

Ala Ala Leu Glu Pro Ser Met Glu Lys Ile Phe Lys Ile Asp Gln Met
65                  70                  75                  80

Gly Arg Trp Phe Val Ala Gly Ala Ala Val Gly Leu Gly Ala Leu
                85                  90                  95

Cys Tyr Tyr Gly Leu Gly Leu Ser Asn Glu Ile Gly Ala Ile Glu Lys
                100                 105                 110

Ala Val Ile Trp Pro Gln Tyr Val Lys Asp Arg Ile His Ser Thr Tyr
            115                 120                 125

Met Tyr Leu Ala Gly Ser Ile Gly Leu Thr Ala Leu Ser Ala Ile Ala
        130                 135                 140

Ile Ser Arg Thr Pro Val Leu Met Asn Phe Met Met Arg Gly Ser Trp
145                 150                 155                 160

Val Thr Ile Gly Val Thr Phe Ala Ala Met Val Gly Ala Gly Met Leu
                165                 170                 175

Val Arg Ser Ile Pro Tyr Asp Gln Ser Pro Gly Pro Lys His Leu Ala
            180                 185                 190

Trp Leu Leu His Ser Gly Val Met Gly Ala Val Ala Pro Leu Thr
        195                 200                 205

Ile Leu Gly Gly Pro Leu Leu Ile Arg Ala Ala Trp Tyr Thr Ala Gly
    210                 215                 220

Ile Val Gly Gly Leu Ser Thr Val Ala Met Cys Ala Pro Ser Glu Lys
225                 230                 235                 240

Phe Leu Asn Met Gly Ala Pro Leu Gly Val Gly Leu Gly Leu Val Phe
                245                 250                 255

Val Ser Ser Leu Gly Ser Met Phe Leu Pro Pro Thr Thr Val Ala Gly
            260                 265                 270

Ala Thr Leu Tyr Ser Val Ala Met Tyr Gly Gly Leu Val Leu Phe Ser
        275                 280                 285

Met Phe Leu Leu Tyr Asp Thr Gln Lys Val Ile Lys Arg Ala Glu Val
    290                 295                 300

Ser Pro Met Tyr Gly Val Gln Lys Tyr Asp Pro Ile Asn Ser Met Leu
305                 310                 315                 320

Ser Ile Tyr Met Asp Thr Leu Asn Ile Phe Met Arg Val Ala Thr Met
                325                 330                 335

Leu Ala Thr Gly Gly Asn Arg Lys Lys
```

```
                    340             345

<210> SEQ ID NO 3
<211> LENGTH: 2992
<212> TYPE: DNA
<213> ORGANISM: Homo sapiens
<220> FEATURE:
<221> NAME/KEY: CDS
<222> LOCATION: (82)..(1710)

<400> SEQUENCE: 3
gtggagatgt atgcagcata cagcagccgc tagttttcct cagcttcaca tcctgggtgt      60 cgggggggctg ccaccttgat c atg gga gtg ccc agt gta gtc agt gcc ata      111
                         Met Gly Val Pro Ser Val Val Ser Ala Ile
                          1               5                  10 cct atc agg gca gat tgt tcc tcc aaa ccc cag ccc ctc ctg cag ggc      159
Pro Ile Arg Ala Asp Cys Ser Ser Lys Pro Gln Pro Leu Leu Gln Gly
             15                  20                  25 cag cct cac ctc tac ttt tcc cct aag ctt ttg tgc cag ctc cgg ggt      207
Gln Pro His Leu Tyr Phe Ser Pro Lys Leu Leu Cys Gln Leu Arg Gly
         30                  35                  40 tcc ttc ttg cct gtc cac tca gcc tgc cct ggt cct ctc cta acc agg      255
Ser Phe Leu Pro Val His Ser Ala Cys Pro Gly Pro Leu Leu Thr Arg
     45                  50                  55 atg ccc cag gca acc act gtt tct ctg cct tta ggt tcc tgg agt ttg      303
Met Pro Gln Ala Thr Thr Val Ser Leu Pro Leu Gly Ser Trp Ser Leu
 60                  65                  70 aca gag gat aga gat gtt tct gga gaa tgg cca cga gct ttc cca gat      351
Thr Glu Asp Arg Asp Val Ser Gly Glu Trp Pro Arg Ala Phe Pro Asp
 75                  80                  85                  90 acc cca cct ggg atg act act agc gtc ttc cct gtt gcc ggt gcc tgc      399
Thr Pro Pro Gly Met Thr Thr Ser Val Phe Pro Val Ala Gly Ala Cys
                 95                 100                 105 cac agt gta aaa agc ctg cag aga caa cgg ggt gcc tcc cca tct cgg      447
His Ser Val Lys Ser Leu Gln Arg Gln Arg Gly Ala Ser Pro Ser Arg
            110                 115                 120 gag aga aaa ccc acg ggg gtg tcg gtg atc tac tgg gag agg ctc ctg      495
Glu Arg Lys Pro Thr Gly Val Ser Val Ile Tyr Trp Glu Arg Leu Leu
        125                 130                 135 cta ggc tca ggc agt ggg caa gcc agc gtc agc ctg cga ctg acc tcc      543
Leu Gly Ser Gly Ser Gly Gln Ala Ser Val Ser Leu Arg Leu Thr Ser
    140                 145                 150 ccg ctt agg cct ccc gag ggc gtc cgg ctt agg gaa aag aca ctc aca      591
Pro Leu Arg Pro Pro Glu Gly Val Arg Leu Arg Glu Lys Thr Leu Thr
155                 160                 165                 170 gag cat gcg ttg ctg ggg agg cag ccc agg acg cct gag cgg cag aaa      639
Glu His Ala Leu Leu Gly Arg Gln Pro Arg Thr Pro Glu Arg Gln Lys
                175                 180                 185 cca tgt gca cag gag gtc cct ggg aga acc ttt ggg agc gcc cag gac      687
Pro Cys Ala Gln Glu Val Pro Gly Arg Thr Phe Gly Ser Ala Gln Asp
            190                 195                 200 ctg gag gct gcc ggc ggt cgg gga cat cac cga atg ggt gca gtt tgg      735
Leu Glu Ala Ala Gly Gly Arg Gly His His Arg Met Gly Ala Val Trp
        205                 210                 215 cag gag cct cat aga ctc ctc ggt ggc cag gag ccc tcg acc tgg gac      783
Gln Glu Pro His Arg Leu Leu Gly Gly Gln Glu Pro Ser Thr Trp Asp
    220                 225                 230 gag ctg ggc gag gct ctt cac gct ggg gag aag tcc ttc gaa tgc agg      831
Glu Leu Gly Glu Ala Leu His Ala Gly Glu Lys Ser Phe Glu Cys Arg
235                 240                 245                 250
```

```
gcg tgc agc aaa gtg ttc gtg aag agc tcc gac ctc ctc aag cac cta      879
Ala Cys Ser Lys Val Phe Val Lys Ser Ser Asp Leu Leu Lys His Leu
            255                 260                 265 cgc acc cac acc ggg gag cgg ccc tac gag tgc gcc cag tgc ggc aag      927
Arg Thr His Thr Gly Glu Arg Pro Tyr Glu Cys Ala Gln Cys Gly Lys
        270                 275                 280 gcc ttc agc cag acg tcg cac ttg acg cag cac cag cgc atc cac agc      975
Ala Phe Ser Gln Thr Ser His Leu Thr Gln His Gln Arg Ile His Ser
            285                 290                 295 ggc gag acg ccc tac gcg tgc ccc gtg tgc ggc aag gcc ttc cgg cat     1023
Gly Glu Thr Pro Tyr Ala Cys Pro Val Cys Gly Lys Ala Phe Arg His
    300                 305                 310 agc tcc tcg ctg gtg cgg cac cag cgc atc cac acg gcc gag aag tcc     1071
Ser Ser Ser Leu Val Arg His Gln Arg Ile His Thr Ala Glu Lys Ser
315                 320                 325                 330 ttc cgc tgc tcc gag tgc ggc aag gcc ttc agc cac ggc tcc aac ctc     1119
Phe Arg Cys Ser Glu Cys Gly Lys Ala Phe Ser His Gly Ser Asn Leu
                335                 340                 345 agc cag cac cgc aag atc cac gcg ggt ggg cgt cct tat gct tgc gca     1167
Ser Gln His Arg Lys Ile His Ala Gly Gly Arg Pro Tyr Ala Cys Ala
            350                 355                 360 cag tgt ggc cgc cgc ttc tgc cgc aac tcg cac ctg atc cag cac gag     1215
Gln Cys Gly Arg Arg Phe Cys Arg Asn Ser His Leu Ile Gln His Glu
        365                 370                 375 cgt acg cac aca ggc gag aag ccc ttc gtg tgc gcg ctc tgc ggt gct     1263
Arg Thr His Thr Gly Glu Lys Pro Phe Val Cys Ala Leu Cys Gly Ala
380                 385                 390 gcc ttc agc cag ggc tcc tcg ctc ttt aag cac cag cgc gtg cac aca     1311
Ala Phe Ser Gln Gly Ser Ser Leu Phe Lys His Gln Arg Val His Thr
395                 400                 405                 410 ggc gag aag ccc ttc gcc tgc cca cag tgc ggc cgc gcc ttt agc cac     1359
Gly Glu Lys Pro Phe Ala Cys Pro Gln Cys Gly Arg Ala Phe Ser His
                415                 420                 425 agc tcc aac ctc acc cag cac cag ctc ctg cac acg ggc gag cgg ccc     1407
Ser Ser Asn Leu Thr Gln His Gln Leu Leu His Thr Gly Glu Arg Pro
            430                 435                 440 ttc cgc tgc gtg gac tgt ggc aag gcc ttc gcc aag ggc gcc gtg ctg     1455
Phe Arg Cys Val Asp Cys Gly Lys Ala Phe Ala Lys Gly Ala Val Leu
        445                 450                 455 ctc agc cac cgg cgc att cac acg ggc gag aag ccc ttc gtg tgt acg     1503
Leu Ser His Arg Arg Ile His Thr Gly Glu Lys Pro Phe Val Cys Thr
460                 465                 470 cag tgt ggc cgc gcc ttc cgt gag cgc ccg gcc ctc ttc cac cac cag     1551
Gln Cys Gly Arg Ala Phe Arg Glu Arg Pro Ala Leu Phe His His Gln
475                 480                 485                 490 agg atc cat acc ggc gag aag acc gtc cgg cga tcc agg gcc agc ctg     1599
Arg Ile His Thr Gly Glu Lys Thr Val Arg Arg Ser Arg Ala Ser Leu
                495                 500                 505 cac ccc cag gcc agg tct gtt gcc ggg gca tca tca gaa ggt gcg cca     1647
His Pro Gln Ala Arg Ser Val Ala Gly Ala Ser Ser Glu Gly Ala Pro
            510                 515                 520 gcg aag gaa acc gag ccc act ccc gcc tcg ggc cca gcc gcc gtc tcg     1695
Ala Lys Glu Thr Glu Pro Thr Pro Ala Ser Gly Pro Ala Ala Val Ser
        525                 530                 535 cag cca gcg gag gtc tgaggtcaca ggttgcagcc ctggccttct gtgaatccct     1750
Gln Pro Ala Glu Val
    540 tccacagcta aagggcatat gtcctctgca gatcccacag caagaaaaag tcccgtgctt   1810 gctagtcagg gacaaggagg ccctttggct gtgatttcat ttgcacgtgg gacaggattt   1870
```

```
gccagttcac ccacagatca cacctccatc cccaaagagg tagcactgca gcaacatcag    1930
ggggaggacg tggtggctga actctagtgg ggccgagact attcagagcc agtaggaggc    1990
cgacagtcac agcactgcac tgtggtgcgg cttcatgtga tatgacagtg gatgctaagg    2050
tgagagggat gcaggcatgg gttgggggtg gcccagagaa acttatgaca gctgtacaca    2110
aactggccgc tggagagatg cccgctgagg gtattctccc ctcaacccac tgcctctgtt    2170
catccaagac ttcctagggg ccagcctagc agacaagaga ccacaaggga ctggggatca    2230
gggtctgggc tctgtcagcc gccacctctg gaaagagaa aaggtttggg tccactgaac    2290
atcatgtttg tagacgctga caggtggggt cctaatgaga gccaacacat gctcactgcc    2350
agctcctgtc ctgagtactg ggaagtttct cctgaagccc tgtgagatgg ctctgtggct    2410
ggtatcccga cttggaagat gaggaaactg aggcacacgg cctggcctgg cttcacacac    2470
atagccgact caggagaggg atgcccatgg gggaacatgt gactctcagc attgaagga    2530 cagagctagg atgatggctt tccggtggca ctcgttcagg ttttgccca agtctcagct    2590 tggccaaggc ctgtcactga ctggtttacc aaagtcgatg tgaggaggag ctttatacc    2650 tgagggatg atgttaactt cagacaagat ggagctgctc acttttgccg ggtttggtgg    2710
ccacttcacc cccaaccctg tctcaccccc attatccctc ctcaattgga ggctggacag    2770
agctgaatag gaaagacttg ctattgccta aggctatgtg tgacaccctc ctgaggacct    2830 ccccaccca gtgtaatggc ccttcatggc agggacagaa aggtggactg ggggccattt    2890
gcttcctgtg gccttcagca gaccaggccc tgtccctacc tggagcctca cctccaagga    2950
aattcatgtt ctccttaatg gaaaaaaaaa aaaaaaaaaa aa                       2992
```

<210> SEQ ID NO 4
<211> LENGTH: 543
<212> TYPE: PRT
<213> ORGANISM: Homo sapiens

<400> SEQUENCE: 4

```
Met Gly Val Pro Ser Val Val Ser Ala Ile Pro Ile Arg Ala Asp Cys
 1               5                  10                  15

Ser Ser Lys Pro Gln Pro Leu Leu Gln Gly Gln Pro His Leu Tyr Phe
            20                  25                  30

Ser Pro Lys Leu Leu Cys Gln Leu Arg Gly Ser Phe Leu Pro Val His
        35                  40                  45

Ser Ala Cys Pro Gly Pro Leu Leu Thr Arg Met Pro Gln Ala Thr Thr
    50                  55                  60

Val Ser Leu Pro Leu Gly Ser Trp Ser Leu Thr Glu Asp Arg Asp Val
65                  70                  75                  80

Ser Gly Glu Trp Pro Arg Ala Phe Pro Asp Thr Pro Gly Met Thr
                85                  90                  95

Thr Ser Val Phe Pro Val Ala Gly Ala Cys His Ser Val Lys Ser Leu
            100                 105                 110

Gln Arg Gln Arg Gly Ala Ser Pro Ser Arg Glu Arg Lys Pro Thr Gly
        115                 120                 125

Val Ser Val Ile Tyr Trp Glu Arg Leu Leu Gly Ser Gly Ser Gly
    130                 135                 140

Gln Ala Ser Val Ser Leu Arg Leu Thr Ser Pro Leu Arg Pro Glu
145                 150                 155                 160

Gly Val Arg Leu Arg Glu Lys Thr Leu Thr Glu His Ala Leu Leu Gly
                165                 170                 175
```

-continued

```
Arg Gln Pro Arg Thr Pro Glu Arg Gln Lys Pro Cys Ala Gln Glu Val
            180                 185                 190
Pro Gly Arg Thr Phe Gly Ser Ala Gln Asp Leu Glu Ala Ala Gly Gly
        195                 200                 205
Arg Gly His His Arg Met Gly Ala Val Trp Gln Glu Pro His Arg Leu
    210                 215                 220
Leu Gly Gln Glu Pro Ser Thr Trp Asp Glu Leu Gly Glu Ala Leu
225                 230                 235                 240
His Ala Gly Glu Lys Ser Phe Glu Cys Arg Ala Cys Ser Lys Val Phe
                245                 250                 255
Val Lys Ser Ser Asp Leu Leu Lys His Leu Arg Thr His Thr Gly Glu
            260                 265                 270
Arg Pro Tyr Glu Cys Ala Gln Cys Gly Lys Ala Phe Ser Gln Thr Ser
        275                 280                 285
His Leu Thr Gln His Gln Arg Ile His Ser Gly Glu Thr Pro Tyr Ala
    290                 295                 300
Cys Pro Val Cys Gly Lys Ala Phe Arg His Ser Ser Ser Leu Val Arg
305                 310                 315                 320
His Gln Arg Ile His Thr Ala Glu Lys Ser Phe Arg Cys Ser Glu Cys
                325                 330                 335
Gly Lys Ala Phe Ser His Gly Ser Asn Leu Ser Gln His Arg Lys Ile
            340                 345                 350
His Ala Gly Gly Arg Pro Tyr Ala Cys Ala Gln Cys Gly Arg Arg Phe
        355                 360                 365
Cys Arg Asn Ser His Leu Ile Gln His Glu Arg Thr His Thr Gly Glu
    370                 375                 380
Lys Pro Phe Val Cys Ala Leu Cys Gly Ala Ala Phe Ser Gln Gly Ser
385                 390                 395                 400
Ser Leu Phe Lys His Gln Arg Val His Thr Gly Glu Lys Pro Phe Ala
                405                 410                 415
Cys Pro Gln Cys Gly Arg Ala Phe Ser His Ser Ser Asn Leu Thr Gln
            420                 425                 430
His Gln Leu Leu His Thr Gly Glu Arg Pro Phe Arg Cys Val Asp Cys
        435                 440                 445
Gly Lys Ala Phe Ala Lys Gly Ala Val Leu Leu Ser His Arg Arg Ile
    450                 455                 460
His Thr Gly Glu Lys Pro Phe Val Cys Thr Gln Cys Gly Arg Ala Phe
465                 470                 475                 480
Arg Glu Arg Pro Ala Leu Phe His His Gln Arg Ile His Thr Gly Glu
                485                 490                 495
Lys Thr Val Arg Arg Ser Arg Ala Ser Leu His Pro Gln Ala Arg Ser
            500                 505                 510
Val Ala Gly Ala Ser Ser Glu Gly Ala Pro Ala Lys Glu Thr Glu Pro
        515                 520                 525
Thr Pro Ala Ser Gly Pro Ala Val Ser Gln Pro Ala Glu Val
    530                 535                 540
```

<210> SEQ ID NO 5
<211> LENGTH: 2046
<212> TYPE: DNA
<213> ORGANISM: Homo sapiens
<220> FEATURE:
<221> NAME/KEY: CDS
<222> LOCATION: (72)..(1892)

```
<400> SEQUENCE: 5
cttggagtga gtggacgcac tcgggaattg taggaggacg aggctcagct cttgccaggc        60
caaattgaga c atg tct gac aca agc gag agt ggt gca ggt cta act cgc       110
            Met Ser Asp Thr Ser Glu Ser Gly Ala Gly Leu Thr Arg
             1               5                  10 ttc cag gct gaa gct tca gaa aag gac agt agc tcg atg atg cag act       158
Phe Gln Ala Glu Ala Ser Glu Lys Asp Ser Ser Ser Met Met Gln Thr
 15                  20                  25 ctg ttg aca gtg acc cag aat gtg gag gtc cca gag aca ccg aag gcc       206
Leu Leu Thr Val Thr Gln Asn Val Glu Val Pro Glu Thr Pro Lys Ala
 30                  35                  40                  45 tca aag gca ctg gag gtc tca gag gat gtg aag gtc tca aaa gcc tct       254
Ser Lys Ala Leu Glu Val Ser Glu Asp Val Lys Val Ser Lys Ala Ser
                 50                  55                  60 ggg gtc tca aag gcc aca gag gtc tca aag acc cca gag gct cgg gag       302
Gly Val Ser Lys Ala Thr Glu Val Ser Lys Thr Pro Glu Ala Arg Glu
             65                  70                  75 gca cct gcc acc cag gcc tcg tct act act cag ctg act gat acc cag       350
Ala Pro Ala Thr Gln Ala Ser Ser Thr Thr Gln Leu Thr Asp Thr Gln
         80                  85                  90 gtt ctg gca gct gaa aac aag agt cta gca gct gac acc aag aaa cag       398
Val Leu Ala Ala Glu Asn Lys Ser Leu Ala Ala Asp Thr Lys Lys Gln
     95                 100                 105 aat gct gac ccg cag gct gtg aca atg cct gcc act gag acc aaa aag       446
Asn Ala Asp Pro Gln Ala Val Thr Met Pro Ala Thr Glu Thr Lys Lys
110                 115                 120                 125 gtc agc cat gtg gct gat acg aag gtc aat aca aag gct cag gag act       494
Val Ser His Val Ala Asp Thr Lys Val Asn Thr Lys Ala Gln Glu Thr
                130                 135                 140 gag gct gca ccc tct cag gcc cca gca gat gaa cct gag cct gag agt       542
Glu Ala Ala Pro Ser Gln Ala Pro Ala Asp Glu Pro Glu Pro Glu Ser
            145                 150                 155 gca gct gcc cag tct cag gag aat cag gat act cgg ccc aag gtc aaa       590
Ala Ala Ala Gln Ser Gln Glu Asn Gln Asp Thr Arg Pro Lys Val Lys
        160                 165                 170 gcc aag aaa gcc cga aag gtg aag cat ctg gat ggg gaa gag gat ggc       638
Ala Lys Lys Ala Arg Lys Val Lys His Leu Asp Gly Glu Glu Asp Gly
    175                 180                 185 agc agt gat cag agt cag gct tct gga acc aca ggt ggc cga agg gtc       686
Ser Ser Asp Gln Ser Gln Ala Ser Gly Thr Thr Gly Gly Arg Arg Val
190                 195                 200                 205 tca aag gct cta atg gcc tca atg gcc cgc agg gct tca agg ggt ccc       734
Ser Lys Ala Leu Met Ala Ser Met Ala Arg Arg Ala Ser Arg Gly Pro
                210                 215                 220 ata gcc ttt tgg gcc cgc agg gca tca agg act cgg gtt ggc tgc ttg       782
Ile Ala Phe Trp Ala Arg Arg Ala Ser Arg Thr Arg Val Gly Cys Leu
            225                 230                 235 ggc ccg gag agc ctt gct ctc ctg aga tca cct aaa gcc cgt agg ggc       830
Gly Pro Glu Ser Leu Ala Leu Leu Arg Ser Pro Lys Ala Arg Arg Gly
        240                 245                 250 aag gct cgc cgt aga gct gcc aag ctc cag tca tcc caa gag cct gaa       878
Lys Ala Arg Arg Arg Ala Ala Lys Leu Gln Ser Ser Gln Glu Pro Glu
    255                 260                 265 gca cca cca cct cgg gat gtg gcc ctt ttg caa ggg agg gca aat gat       926
Ala Pro Pro Pro Arg Asp Val Ala Leu Leu Gln Gly Arg Ala Asn Asp
270                 275                 280                 285 ttg gtg aag tac ctt ttg gct aaa gac cag acg aag att ccc atc aag       974
Leu Val Lys Tyr Leu Leu Ala Lys Asp Gln Thr Lys Ile Pro Ile Lys
                290                 295                 300
```

-continued

```
cgc tcg gac atg ctg aag gac atc atc aaa gaa tac act gat gtg tac      1022
Arg Ser Asp Met Leu Lys Asp Ile Ile Lys Glu Tyr Thr Asp Val Tyr
            305                 310                 315 ccc gaa atc att gaa cga gca ggc tat tct ttg gag aag gta ttt ggg      1070
Pro Glu Ile Ile Glu Arg Ala Gly Tyr Ser Leu Glu Lys Val Phe Gly
        320                 325                 330 att caa ttg aag gaa att gat aag aat gac cac ttg tac att ctt ctc      1118
Ile Gln Leu Lys Glu Ile Asp Lys Asn Asp His Leu Tyr Ile Leu Leu
    335                 340                 345 agc acc tta gag ccc act gat gca ggc ata ctg gga acg act aag gac      1166
Ser Thr Leu Glu Pro Thr Asp Ala Gly Ile Leu Gly Thr Thr Lys Asp
350                 355                 360                 365 tca ccc aag ctg ggt ctg ctc atg gtg ctt ctt agc atc atc ttc atg      1214
Ser Pro Lys Leu Gly Leu Leu Met Val Leu Leu Ser Ile Ile Phe Met
                370                 375                 380 aat gga aat cgg tcc agt gag gct gtc atc tgg gag gtg ctg cgc aag      1262
Asn Gly Asn Arg Ser Ser Glu Ala Val Ile Trp Glu Val Leu Arg Lys
            385                 390                 395 ttg ggg ctg cgc cct ggg ata cat cat tca ctc ttt ggg gac gtg aag      1310
Leu Gly Leu Arg Pro Gly Ile His His Ser Leu Phe Gly Asp Val Lys
        400                 405                 410 aag ctc atc act gat gag gtt gtg aag cag aag tac ctg gac tat gcc      1358
Lys Leu Ile Thr Asp Glu Val Val Lys Gln Lys Tyr Leu Asp Tyr Ala
    415                 420                 425 aga gtc ccc aat agc aat ccc cct gaa tat gag ttc ttc tgg ggc ctg      1406
Arg Val Pro Asn Ser Asn Pro Pro Glu Tyr Glu Phe Phe Trp Gly Leu
430                 435                 440                 445 cgc tct tac tat gag acc agc aag atg aaa gtc ctc aag ttt gcc tgc      1454
Arg Ser Tyr Tyr Glu Thr Ser Lys Met Lys Val Leu Lys Phe Ala Cys
                450                 455                 460 aag gta caa aag aag gat ccc aag gaa tgg gca gct cag tac cga gag      1502
Lys Val Gln Lys Lys Asp Pro Lys Glu Trp Ala Ala Gln Tyr Arg Glu
            465                 470                 475 gcg atg gaa gcg gat ttg aag gct gca gct gag gct gca gct gaa gcc      1550
Ala Met Glu Ala Asp Leu Lys Ala Ala Ala Glu Ala Ala Ala Glu Ala
        480                 485                 490 aag gct agg gcc gag att aga gct cga atg ggc att ggg ctc ggc tcg      1598
Lys Ala Arg Ala Glu Ile Arg Ala Arg Met Gly Ile Gly Leu Gly Ser
    495                 500                 505 gag aat gct gcc ggg ccc tgc aac tgg gac gaa gct gat atc gga ccc      1646
Glu Asn Ala Ala Gly Pro Cys Asn Trp Asp Glu Ala Asp Ile Gly Pro
510                 515                 520                 525 tgg gcc aaa gcc cgg atc cag gcg gga gca gaa gct aaa gcc aaa gcc      1694
Trp Ala Lys Ala Arg Ile Gln Ala Gly Ala Glu Ala Lys Ala Lys Ala
                530                 535                 540 caa gag agt ggc agt gcc agc act ggt gcc agt acc agt acc aat aac      1742
Gln Glu Ser Gly Ser Ala Ser Thr Gly Ala Ser Thr Ser Thr Asn Asn
            545                 550                 555 agt gcc agt gcc agt gcc agc acc agt ggt ggc ttc agt gct ggt gcc      1790
Ser Ala Ser Ala Ser Ala Ser Thr Ser Gly Gly Phe Ser Ala Gly Ala
        560                 565                 570 agc ctg acc gcc act ctc aca ttt ggg ctc ttc gct ggc ctt ggt gga      1838
Ser Leu Thr Ala Thr Leu Thr Phe Gly Leu Phe Ala Gly Leu Gly Gly
    575                 580                 585 gct ggt gcc agc acc agt ggc agc tct ggt gcc tgt ggt ttc tcc tac      1886
Ala Gly Ala Ser Thr Ser Gly Ser Ser Gly Ala Cys Gly Phe Ser Tyr
590                 595                 600                 605 aag tga gattttagat attgttaatc ctgccagtct ttctcttcaa gccagggtgc      1942
Lys
```

-continued atcctcagaa acctactcaa cacagcactc taggcagcca ctatcaatca attgaagttg    2002
acactctgca ttaaatctat ttgccaaaaa aaaaaaaaaa aaaa    2046

<210> SEQ ID NO 6
<211> LENGTH: 606
<212> TYPE: PRT
<213> ORGANISM: Homo sapiens

<400> SEQUENCE: 6

Met Ser Asp Thr Ser Glu Ser Gly Ala Gly Leu Thr Arg Phe Gln Ala
 1               5                  10                  15

Glu Ala Ser Glu Lys Asp Ser Ser Met Met Gln Thr Leu Leu Thr
            20                  25                  30

Val Thr Gln Asn Val Glu Val Pro Glu Thr Pro Lys Ala Ser Lys Ala
        35                  40                  45

Leu Glu Val Ser Glu Asp Val Lys Val Ser Lys Ala Ser Gly Val Ser
    50                  55                  60

Lys Ala Thr Glu Val Ser Lys Thr Pro Glu Ala Arg Glu Ala Pro Ala
65                  70                  75                  80

Thr Gln Ala Ser Ser Thr Thr Gln Leu Thr Asp Thr Gln Val Leu Ala
                85                  90                  95

Ala Glu Asn Lys Ser Leu Ala Ala Asp Thr Lys Lys Gln Asn Ala Asp
            100                 105                 110

Pro Gln Ala Val Thr Met Pro Ala Thr Glu Thr Lys Lys Val Ser His
        115                 120                 125

Val Ala Asp Thr Lys Val Asn Thr Lys Ala Gln Glu Thr Glu Ala Ala
    130                 135                 140

Pro Ser Gln Ala Pro Ala Asp Glu Pro Glu Pro Glu Ser Ala Ala Ala
145                 150                 155                 160

Gln Ser Gln Glu Asn Gln Asp Thr Arg Pro Lys Val Lys Ala Lys Lys
                165                 170                 175

Ala Arg Lys Val Lys His Leu Asp Gly Glu Glu Asp Gly Ser Ser Asp
            180                 185                 190

Gln Ser Gln Ala Ser Gly Thr Thr Gly Gly Arg Arg Val Ser Lys Ala
        195                 200                 205

Leu Met Ala Ser Met Ala Arg Arg Ala Ser Arg Gly Pro Ile Ala Phe
    210                 215                 220

Trp Ala Arg Arg Ala Ser Arg Thr Arg Val Gly Cys Leu Gly Pro Glu
225                 230                 235                 240

Ser Leu Ala Leu Leu Arg Ser Pro Lys Ala Arg Arg Gly Lys Ala Arg
                245                 250                 255

Arg Arg Ala Ala Lys Leu Gln Ser Ser Gln Glu Pro Glu Ala Pro Pro
            260                 265                 270

Pro Arg Asp Val Ala Leu Leu Gln Gly Arg Ala Asn Asp Leu Val Lys
        275                 280                 285

Tyr Leu Leu Ala Lys Asp Gln Thr Lys Ile Pro Ile Lys Arg Ser Asp
    290                 295                 300

Met Leu Lys Asp Ile Ile Lys Glu Tyr Thr Asp Val Tyr Pro Glu Ile
305                 310                 315                 320

Ile Glu Arg Ala Gly Tyr Ser Leu Glu Lys Val Phe Gly Ile Gln Leu
                325                 330                 335

Lys Glu Ile Asp Lys Asn Asp His Leu Tyr Ile Leu Ser Thr Leu
            340                 345                 350

```
                                          -continued

Glu Pro Thr Asp Ala Gly Ile Leu Gly Thr Thr Lys Asp Ser Pro Lys
        355                 360                 365

Leu Gly Leu Leu Met Val Leu Leu Ser Ile Ile Phe Met Asn Gly Asn
    370                 375                 380

Arg Ser Ser Glu Ala Val Ile Trp Glu Val Leu Arg Lys Leu Gly Leu
385                 390                 395                 400

Arg Pro Gly Ile His His Ser Leu Phe Gly Asp Val Lys Lys Leu Ile
                405                 410                 415

Thr Asp Glu Val Val Lys Gln Lys Tyr Leu Asp Tyr Ala Arg Val Pro
            420                 425                 430

Asn Ser Asn Pro Pro Glu Tyr Glu Phe Phe Trp Gly Leu Arg Ser Tyr
        435                 440                 445

Tyr Glu Thr Ser Lys Met Lys Val Leu Lys Phe Ala Cys Lys Val Gln
    450                 455                 460

Lys Lys Asp Pro Lys Glu Trp Ala Ala Gln Tyr Arg Glu Ala Met Glu
465                 470                 475                 480

Ala Asp Leu Lys Ala Ala Ala Glu Ala Ala Ala Glu Ala Lys Ala Arg
                485                 490                 495

Ala Glu Ile Arg Ala Arg Met Gly Ile Gly Leu Gly Ser Glu Asn Ala
            500                 505                 510

Ala Gly Pro Cys Asn Trp Asp Glu Ala Asp Ile Gly Pro Trp Ala Lys
        515                 520                 525

Ala Arg Ile Gln Ala Gly Ala Glu Ala Lys Ala Lys Ala Gln Glu Ser
    530                 535                 540

Gly Ser Ala Ser Thr Gly Ala Ser Thr Ser Thr Asn Asn Ser Ala Ser
545                 550                 555                 560

Ala Ser Ala Ser Thr Ser Gly Gly Phe Ser Ala Gly Ala Ser Leu Thr
                565                 570                 575

Ala Thr Leu Thr Phe Gly Leu Phe Ala Gly Leu Gly Gly Ala Gly Ala
            580                 585                 590

Ser Thr Ser Gly Ser Ser Gly Ala Cys Gly Phe Ser Tyr Lys
        595                 600                 605

<210> SEQ ID NO 7
<211> LENGTH: 27
<212> TYPE: DNA
<213> ORGANISM: Homo sapiens

<400> SEQUENCE: 7 taccoctacg acgtgcccga ctacgcc                                       27
```